US011351125B2

(12) United States Patent
Zhang et al.

(10) Patent No.: US 11,351,125 B2
(45) Date of Patent: Jun. 7, 2022

(54) POLY(N-BUTYL CYANOACRYLATE) NANOPARTICLE WITH DUAL MODIFICATIONS, PREPARATION METHOD AND USE THEREOF

(71) Applicant: Xuanwu Hospital of Capital Medical University, Beijing (CN)

(72) Inventors: Lan Zhang, Beijing (CN); Xiao Hu, Beijing (CN); Lin Li, Beijing (CN)

(73) Assignee: Xuanwu Hospital of Capital Medical University, Beijing (CN)

( * ) Notice: Subject to any disclaimer, the term of this patent is extended or adjusted under 35 U.S.C. 154(b) by 0 days.

(21) Appl. No.: 16/079,698

(22) PCT Filed: Feb. 21, 2017

(86) PCT No.: PCT/CN2017/074268
§ 371 (c)(1),
(2) Date: Nov. 28, 2018

(87) PCT Pub. No.: WO2017/143967
PCT Pub. Date: Aug. 31, 2017

(65) Prior Publication Data
US 2019/0117582 A1 Apr. 25, 2019

(30) Foreign Application Priority Data

Feb. 24, 2016 (CN) .......................... 201610099924.0

(51) Int. Cl.
*A61K 9/14* (2006.01)
*A61K 47/32* (2006.01)
*A61K 9/51* (2006.01)
*A61K 49/00* (2006.01)
*A61P 25/00* (2006.01)
*A61K 31/337* (2006.01)
*A61K 47/42* (2017.01)
*A61K 47/34* (2017.01)

(52) U.S. Cl.
CPC .............. *A61K 9/5138* (2013.01); *A61K 9/14* (2013.01); *A61K 9/5123* (2013.01); *A61K 9/5146* (2013.01); *A61K 9/5192* (2013.01); *A61K 31/337* (2013.01); *A61K 49/0039* (2013.01); *A61K 49/0093* (2013.01); *A61P 25/00* (2018.01); *A61K 47/34* (2013.01); *A61K 47/42* (2013.01)

(58) Field of Classification Search
None
See application file for complete search history.

(56) References Cited

U.S. PATENT DOCUMENTS

2012/0027821 A1* 2/2012 Shirotake ............. A61K 9/5138
424/400

FOREIGN PATENT DOCUMENTS

| CN | 1582902 A | 2/2005 |
|---|---|---|
| CN | 1850032 A | 10/2006 |
| CN | 101138636 A | 3/2008 |
| CN | 101155549 A | 4/2008 |
| CN | 101579356 A | 11/2009 |
| CN | 104371006 A | 2/2015 |

OTHER PUBLICATIONS

Lähde, Anna, Janne Raula, and Esko I. Kauppinen. "Simultaneous synthesis and coating of salbutamol sulphate nanoparticles with l-leucine in the gas phase." International journal of pharmaceutics 358.1-2 (2008): 256-262. (Year: 2008).*
Huang, Chi-Yu, Chih-Ming Chen, and Yu-Der Lee. "Synthesis of high loading and encapsulation efficient paclitaxel-loaded poly (n-butyl cyanoacrylate) nanoparticles via miniemulsion.";International journal of pharmaceutics 338.1-2 (2007): 267-275. (Year: 2007).*
Das, Debanjan, and Senshang Lin. "Double-coated poly (butylcynanoacrylate) nanoparticulate delivery systems for brain targeting of dalargin via oral administration." Journal of pharmaceutical sciences 94.6 (2005): 1343-1353. (Year: 2005).*
Weiss CK, Lorenz MR, Landfester K, Mailänder V. Cellular uptake behavior of unfunctionalized and functionalized PBCA particles prepared in a miniemulsion. Macromolecular bioscience. Jul. 9, 2007;7(7):883-96. (Year: 2007).*
Chan JM, Zhang L, Yuet KP, Liao G, Rhee JW, Langer R, Farokhzad OC. PLGA-lecithin-PEG core-shell nanoparticles for controlled drug delivery. Biomaterials. Mar. 1, 2009;30(8):1627-34. (Year: 2009).*
de Oliveira Junior ER, Santos LC, Salomão MA, Nascimento TL, Oliveira GD, Lião LM, Lima EM. Nose-to-brain drug delivery mediated by polymeric nanoparticles: influence of PEG surface coating. Drug Delivery and Translational Research. Dec. 2020;10(6):1688-99. (Year: 2020).*
Etame AB, Smith CA, Chan WC, Rutka JT. Design and potential application of PEGylated gold nanoparticles with size-dependent permeation through brain microvasculature. Nanomedicine: Nanotechnology, Biology and Medicine. Dec. 1, 2011;7(6):992-1000. (Year: 2011).*
Xie F, Yao N, Qin Y, Zhang Q, Chen H, Yuan M, Tang J, Li X, Fan W, Zhang Q, Wu Y. Investigation of glucose-modified liposomes using polyethylene glycols with different chain lengths as the linkers for brain targeting. International journal of nanomedicine. 2012;7:163. (Year: 2012).*
Agrawal U, Chashoo G, Sharma PR, Kumar A, Saxena AK, Vyas SP. Tailored polymer-lipid hybrid nanoparticles for the delivery of drug conjugate: dual strategy for brain targeting. Colloids and Surfaces B: Biointerfaces. Feb. 1, 2015;126:414-25. (Year: 2015).*

(Continued)

*Primary Examiner* — Nissa M Westerberg
(74) *Attorney, Agent, or Firm* — Wolf, Greenfield & Sacks, P.C.

(57) ABSTRACT

The invention relates to a poly(n-butyl cyanoacrylate) nanoparticle with dual modifications, a drug delivery system comprising the nanoparticle, and a method for preparing the nanoparticle or the drug delivery system. The nanoparticle is modified with a first modifier and a second modifier on the surface, the first modifier is a hydrophilic polymer, and the second modifier is an amino acid and/or a lipid. The invention further relates to a use of the nanoparticle in promoting drug penetration across the blood brain barrier in a subject.

15 Claims, 11 Drawing Sheets

(56) References Cited

OTHER PUBLICATIONS

International Search Report and Written Opinion for PCT/CN2017/074268, dated May 24, 2017.
Chai et al., Chinese Pharmaceutical Journal, vol. 44, No. 8, Apr. 30, 2009 (Apr. 30, 2009), ISSN: 1001-2494, p. 562, section 2.
Deb Anjan et al., Double-Coated Poly (Butylcynanoacrylate) Nanoparticulate Delivery Systems for Brain Targeting of Dalargin Via Oral Administration. Journal of Pharmaceutical Sciences, vol. 94, No. 6, Jun. 30, 2005 (Jun. 30, 2005) ISSN: 0022-3549, p. 1345, the left column, paragraph 2 to the right column, paragraph 2.
Xu et al., Efficacy of Amphotericin B-polybutylcyanoacrylate Nanoparticles against Cryptococcal Meningitis in Mice Chinese Journal of Biomedical Engineering, vol. 28, No. 2, Apr. 30, 2009 (Apr. 30, 2009), ISSN: 0258-8021, section 1.2.1.
Chinese Office Action dated Jan. 16, 2020 in connection with CN Patent Application No. 201710092816.5.
Wang et al., Research progress on brain-targeted nano-carrier systems, Chinese Journal of Biochemical Pharmaceutics. Dec. 2008; 355-8.

\* cited by examiner

POLY(N-BUTYL CYANOACRYLATE) NANOPARTICLE WITH DUAL MODIFICATIONS, PREPARATION METHOD AND USE THEREOF

RELATED APPLICATIONS

This application is a national stage filing under 35 U.S.C. 371 of International Patent Application Serial No. PCT/CN2017/074268, filed Feb. 21, 2017, which claims priority to Chinese application number 201610099924.0, filed Feb. 24, 2016, the contents of each of which are incorporated herein by reference in their entirety.

TECHNICAL FIELD

The invention relates to a poly(n-butyl cyanoacrylate) nanoparticle with dual modifications, a drug delivery system comprising the nanoparticle, use of the nanoparticle for manufacture of a drug delivery system, and a method for preparing the nanoparticle and the drug delivery system. The invention further relates to a pharmaceutical composition comprising the drug delivery system, and use of the nanoparticle or drug delivery system for manufacture of a pharmaceutical composition for diagnosing, preventing and/or treating a central nervous system disease in a subject.

BACKGROUND ART

In current, since the incidence rate of central nervous system diseases increases year by year, it has become a major social problem that affects the health level and life quality of people. Poor blood-brain barrier (BBB) permeability is one of the important problems present in drugs for diagnosis or treatment of central nervous system diseases. After systemic administration, most of the drugs can hardly penetrate across the BBB so as to reach an effective therapeutic concentration in the brain, which affects the diagnostic or therapeutic effects of drugs. The problem needs to be solved urgently is how to enhance the BBB permeability of drugs whilst ensuring their safety and effectiveness in vivo.

BBB is formed mainly by tightly-bound brain capillary endothelial cells, and is a barrier structure between blood and central nervous system. On one hand, BBB plays a role in protecting nerves and can ensure the central nervous system to be less invaded by foreign substances. However, the compact structure of BBB also prevents the entry of drugs for diagnosis or treatment of brain diseases into the brain by non-invasive administration route, which restricts the effective diagnosis or treatment of brain diseases with the drugs. It is reported that 100% of large-molecule drugs and 98% of small-molecule drugs cannot cross BBB to arrive at the brain tissue.

Poly(n-butyl cyanoacrylate) (PBCA) nanoparticles (NPs) have good degradability and biocompatibility and have no immunogenicity, and can carry different drugs. However, common PBCA nanoparticles do not have significant BBB permeability. It has been reported in literatures that a PBCA nanoparticle is modified with surfactant Tween-80 on the surface so as to enhance the BBB permeability of the PBCA nanoparticle. However, this method has the following shortcomings: in terms of drug safety, Tween-80 may cause hemolysis after intravenous administration; when Tween-80 is used to increase the BBB permeability of nanoparticles, it might result in an increased exposure of Tween-80 in the brain, thereby causing toxicity; in addition, upon intravenous administration, nanoparticles modified with Tween-80 alone are easily recognized and phagocytosed by macrophages in the reticuloendothelial system, and therefore the in vivo circulation time of nanoparticle is too short, and the targeting effect is not ideal.

Polyethylene glycol (PEG), which is the most widely used material for modification of nanoparticle surfaces at home and abroad, can prevent the adsorption of protein, and meanwhile protect nanoparticles from being captured by the reticuloendothelial system, thereby prolonging the in vivo circulation time of nanoparticles and enhancing the sustained release of nanoparticles. However, since PEG has strong hydrophilicity, modification of nanoparticles with PEG alone does not facilitate the passage of nanoparticles through the lipidic blood-brain barrier. As a result, the nanoparticles have poor brain-targeting property and poor BBB permeability in vivo, and cannot be used as a good brain-targeting carrier.

Therefore, there is need in this field to develop a drug carrier having higher BBB permeability, higher safety, and good sustained-release property, for the diagnosis, prevention and/or treatment of a central nervous system disease.

Contents of Invention

In the invention, unless otherwise specified, the scientific and technical terms used herein have the meanings as generally understood by a person skilled in the art. Moreover, the laboratory operations used herein are the routine operations widely used in the corresponding fields. However, in order to understand the invention better, definitions and explanations are provided for relevant terms.

As used herein, the term "poly(n-butyl cyanoacrylate)" refers to a polymer obtained by the polymerization of n-butyl cyanoacrylate as a monomer, wherein the n-butyl cyanoacrylate has the following structure:

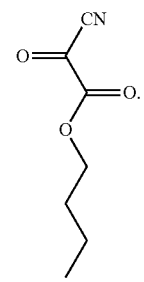

As used herein, the term "nanoparticles" refer to particles with a particle size on the order of nanometer, for example, particles with a particle size of no greater than 1000 nm, such as particles with a particle size between 50 and 800 nm.

As used herein, the term "particle size", i.e. "an equivalent particle size", means that when a certain physical property or physical behavior of a particle to be measured is most similar to that of a homogeneous sphere (or combination) with a certain diameter, the diameter of the sphere (or combination) is taken as the equivalent particle size (or particle size distribution) of the particle to be measured.

As used herein, the term "an average particle size" means that when an actual particle population consisting of particles with different sizes and shapes is compared with a hypothetical particle population consisting of uniform spherical particles, if the two particle populations have the same particle diameters in full length, the diameter of the spherical particle is called the average particle size of the actual particle population. Methods for measuring an average particle size are known to those skilled in the art, for example, light scattering method; and apparatuses for measuring an average particle size include, but are not limited to Light Scattering Particle Size Analyzer.

As used herein, the term "emulsion polymerization" refers to the polymerization of monomers that are dispersed in a medium to form an emulsion. Generally, monomers are dispersed under mechanical stirring in the presence of a stabilizer to form monomer droplets, and are subjected to a polymerization reaction to form polymer particles having a particle size that may be on the order of micrometer or nanometer. For example, in the invention, n-butyl cyanoacrylate can form polycyanoacrylate nanoparticles by emulsion polymerization in an acidic medium (e.g. a hydrochloric acid solution). Modifiers may be added to the polymerization reaction system to obtain polymer particles with modification on surface.

As used herein, the term "stabilizer" refers to a substance that can maintain or enhance the stability of particles. In emulsion polymerization, a stabilizer can form a protective layer on the surface of monomer droplets or polymer particles so as to prevent aggregation and to stabilize the emulsion. The stabilizer includes, but is not limited to cyclodextrin (e.g. Dex70), polyvinyl pyrrolidone (e.g. PVP-K30) and poloxamer (e.g. Poloxamer F68).

As used herein, the term "a hydrophilic polymer" refers to a polymer with polar groups, which has a high affinity for water, can attract water molecules and/or be dissolved in water. The hydrophilic polymer includes polymers that can be dissolved or swollen in water, such as polyethylene glycol, polyacrylamide, polyvinyl pyrrolidone, polyvinyl alcohol and carboxymethyl cellulose.

As used herein, the term "lipids" refer to organic compounds that are not soluble in water but soluble in non-polar organic solvents (e.g. chloroform, ether, acetone, or benzene, etc.), for example, phospholipids (e.g. glycerophosphate and sphingomyelin) and sterols.

As used herein, the term "glycerophosphate" refers to a class of compounds having the following structure:

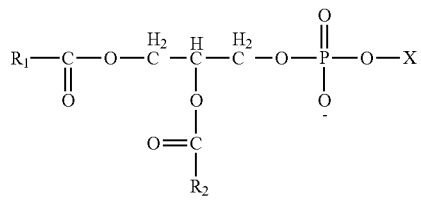

wherein, $R_1$ and $R_2$ represent the hydrocarbon chain of fatty acids, and X represents hydrogen or a polar substituent. The glycerophosphate includes, but is not limited to, lecithin (phosphatidylcholine), cephalin (phosphatidylethanolamine), phosphatidylserine, and phosphatidylinositol.

As used herein, the term "lecithin" refers to an example of glycerophosphate in which X is —$CH_2CH_2N^+(CH_3)_3$, $R_1$ is generally a saturated hydrocarbon chain (e.g. a saturated hydrocarbon chain containing 16-18 carbon atoms), and $R_2$ is generally an unsaturated hydrocarbon chain, e.g. a hydrocarbon chain of arachidonic acid ($CH_3(CH_2)_4(CH=CH-CH_2)_4(CH_2)_2$—).

As used herein, the term "sterols", also known as steroid alcohols, refer to compounds having perhydrocyclopentanophenanthrene as a basic structure and comprising an alcoholic hydroxyl, including, but not limited to zoosterols (e.g. cholesterol), phytosterols and fungisterols.

As used herein, the term "cholesterol" refers to a compound having the following structure:

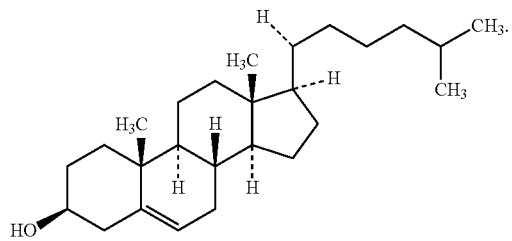

As used herein, the term "amino acid" refers to an amino-containing carboxylic acid, including but not limited to: aliphatic amino acids, such as alanine, leucine, valine and aspartic acid; aromatic amino acids, such as phenylalanine and tyrosine; heterocyclic amino acids, such as histidine and tryptophan; and heterocyclic imino acids, such as proline.

As used herein, the term "polyethylene glycol (PEG)" refers to a polymer having —$CH_2CH_2O$— as a repeat unit, which has a number-average molecular weight of above 200, e.g. 200~20000. In the molecular chain of the polyethylene glycol, both of the terminal groups are hydroxyl, or one terminal group is hydroxyl, and the other terminal group is methoxy (i.e. methoxy polyethylene glycol, mPEG). Polyethylene glycol with a number-average molecular weight of 100000~1000000 is also called polyethylene oxide (PEO). In the invention, polyethylene glycol and polyethylene oxide have the same meanings.

As used herein, the term "polyvinyl alcohol (PVA)" refers to a polymer having —$CH_2CH(OH)$— as a repeat unit.

As used herein, the term "polyvinyl pyrrolidone (PVP)" refers to a polymer having the following repeat unit:

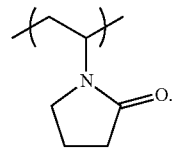

As used herein, the term "coumarin-6" refers to a compound having the following structure:

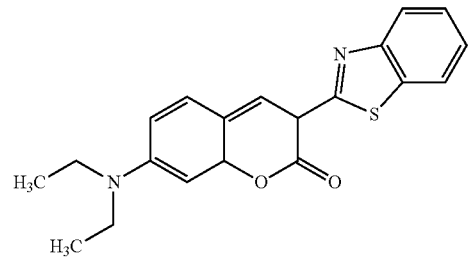

As used herein, the term "entrapment efficiency" is used to characterize the drug-entrapping capability of a drug delivery system. In the invention, entrapment efficiency is calculated by the formula: the amount of drug entrapped in a nanoparticle/(the amount of drug entrapped in a nanoparticle+the amount of drug unentrapped in a nanoparticle)×100%.

As used herein, the term "a drug loading rate" is used to characterize the amount of drug contained in a drug delivery system. In the invention, a drug loading rate is calculated by the formula: the mass of drug in a drug-loaded nanoparticle/ (the mass of drug in a drug-loaded nanoparticle+the mass of a nanoparticle for drug loading)×100%.

As used herein, the term "room temperature" refers to 25±5° C.

As used herein, the term "about" should be understood by a person skilled in the art, and varies to a certain extent depending on the context. If the use of the term is not clear for a person skilled in the art based the context, the term "about" means no more than ±10% of the specific numerical value or range.

By conducting deep research and paying creative work, the inventor obtained a poly(n-butyl cyanoacrylate) nanoparticle with dual modifications, and a drug delivery system comprising the nanoparticle. The nanoparticle can be used as a brain-targeting delivery system of drug, has good safety, sustained-release property and BBB permeability, can effectively enhance the concentration of drug in the brain, and enables the sustained release of drug so as to prolong the in vivo circulation time. Therefore, the invention is provided as follows.

In one aspect, the invention provides a nanoparticle, comprising or mainly consisting of poly(n-butyl cyanoacrylate), wherein the nanoparticle is modified with a first modifier and a second modifier on the surface, the first modifier is a hydrophilic polymer, and the second modifier is an amino acid and/or a lipid.

In one preferred embodiment, the amino acid is L-amino acid.

In one preferred embodiment, the amino acid is aspartic acid or leucine.

In one preferred embodiment, the lipid is selected from the group consisting of phospholipids (e.g. lecithin) and sterols (e.g. cholesterol).

In the invention, preferably, the amino acid and the lipid are an amino acid and a lipid that are naturally occurring in a subject (e.g. a mammal, such as a bovine, an equine, a caprid, a suidae, a canine, a feline, a rodent and a primate; for example, a human). However, the invention does not limit the source of the amino acid and the lipid, which can be extracted from a subject or be synthesized artificially.

In one preferred embodiment, the hydrophilic polymer is selected from the group consisting of polyethylene glycol, polyvinyl alcohol and polyvinyl pyrrolidone; and preferably, is polyethylene glycol.

In one preferred embodiment, the hydrophilic polymer has a number-average molecular weight of 2000~20000, e.g. 2000~5000, 5000~10000, 10000~15000 or 15000~20000, e.g. 2000, 5000, 10000, 15000 or 20000.

In one preferred embodiment, the nanoparticle has an average particle size of 50~800 nm, e.g. 50~100 nm, 100~400 nm, 400~600 nm or 600~800 nm.

In one preferred embodiment, the nanoparticle has a polydispersity index (PDI) of 0.100~0.300, e.g. 0.100~0.200 or 0.200~0.300.

In one preferred embodiment, the nanoparticle has a Zeta potential of −100~0 mV, e.g. −100~−70 mV, −80~−40 mV, −60~−10 mV or −40~0 mV.

In one preferred embodiment, the first modifier and the polycyanoacrylate have a mass ratio of 0.5%~5%, e.g. 0.5%~1%, 1%~2%, 2%~3%, 3%~4% or 4%~5%.

In one preferred embodiment, the second modifier and the polycyanoacrylate have a mass ratio of 0.05%~2%, e.g. 0.05%~0.1%, 0.1%~0.5%, 0.5%~1%, 1%~1.5% or 1.5%~2%.

In one preferred embodiment, the concentration of the second modifier on the surface of the nanoparticle is $5\times10^{-7}$ ng/nanoparticle~$1\times10^{-6}$ ng/nanoparticle, e.g. $5\times10^{-7}$ ng/nanoparticle~$6\times10^{-7}$ ng/nanoparticle, $6\times10^{-7}$ ng/nanoparticle~$7\times10^{-7}$ ng/nanoparticle, $7\times10^{-7}$ ng/nanoparticle~$8\times10^{-7}$ ng/nanoparticle, $8\times10^{-7}$ ng/nanoparticle~$9\times10^{-7}$ ng/nanoparticle or $9\times10^{-7}$ ng/nanoparticle~$1\times10^{-6}$ ng/nanoparticle.

In one preferred embodiment, the nanoparticle comprises or mainly consists of poly(n-butyl cyanoacrylate), the nanoparticle is modified with a first modifier and a second modifier on the surface, the first modifier is polyethylene glycol, and the second modifier is selected from the group consisting of lecithin, cholesterol, aspartic acid and leucine.

In one preferred embodiment, the polyethylene glycol has a number-average molecular weight of 10000~20000.

In one preferred embodiment, the nanoparticle has an average particle size of 100~400 nm.

In one preferred embodiment, the nanoparticle has a Zeta potential of −40~0 mV.

Optionally, the nanoparticle according to the invention further comprises a stabilizer, for example, the stabilizer is selected from the group consisting of cyclodextrin (e.g. Dex70), polyvinyl pyrrolidone (e.g. PVP-K30) and poloxamer (e.g. Poloxamer F68).

In one preferred embodiment, the nanoparticle is prepared by a method comprising the following steps:

Step 1: n-butyl cyanoacrylate monomers are subjected to a polymerization reaction in an acidic medium comprising a first modifier; preferably, the acidic medium further comprises a stabilizer;

Step 2: a base is added to the reaction mixture of Step 1 until the reaction mixture is neutral, the reaction mixture is filtrated, and the filtrate is lyophilized;

Step 3: the lyophilized product is dispersed in a buffer, a second modifier is added, and incubation is performed; and Step 4: nanoparticles are separated from the mixture of Step 3; preferably, the separation includes filtration and/or lyophilization.

In one preferred embodiment, in Step 1, the n-butyl cyanoacrylate monomer and the acidic medium have a mass/volume ratio of 0.05%~1% g/ml, e.g. 0.05%~0.1% g/ml, 0.1%~0.5% g/ml, 0.1%~0.75% g/ml or 0.75%~1% g/ml.

In one preferred embodiment, in Step 1, the first modifier and the acidic medium have a mass/volume ratio of 0.5%~5% g/ml, e.g. 0.5%~1% g/ml, 0.5%~2% g/ml, 1%~3% g/ml or 3%~5% g/ml.

In one preferred embodiment, in Step 1, the stabilizer and the acidic medium have a mass/volume ratio of 0.05%~5% g/ml, e.g. 0.5%~1% g/ml, 0.5%~2% g/ml, 1%~3% g/ml or 3%~5% g/ml.

In one preferred embodiment, in Step 1, the stabilizer is selected from the group consisting of cyclodextrin (e.g. Dex70), polyvinyl pyrrolidone (e.g. PVP-K30) and poloxamer (e.g. Poloxamer F68).

In one preferred embodiment, the acidic medium is a hydrochloric acid solution; preferably, the hydrochloric acid solution has a pH of 1.0~3.0.

In one preferred embodiment, the polymerization reaction is carried out at room temperature.

In one preferred embodiment, the polymerization reaction in Step 1 is carried out for 1~10 h, e.g. 1~5 h, 2~6 h, 3~7 h, 4~8 h or 5~10 h.

In one preferred embodiment, in Step 2, the base is sodium hydroxide.

In one preferred embodiment, in Step 2, filtration is performed by using a filtration membrane, preferably, filtration is performed by using a filtration membrane with a pore size of 0.45 μm.

In one preferred embodiment, in Step 3, the buffer is a phosphate buffer.

In one preferred embodiment, in Step 3, the second modifier and the buffer have a mass/volume ratio of 0.05%~2% g/ml, e.g. 0.05%~0.1% g/ml, 0.1%~0.5% g/ml, 0.5%~1% g/ml or 1%~2%.

In one preferred embodiment, in Step 3, incubation is performed for 0.5~5 h, e.g. 0.5~1 h, 1~2 h, 2~3 h, 3~4 h or 4~5 h.

In one aspect, the invention provides a method for preparing the nanoparticle as described above, comprising the following steps:

Step 1: n-butyl cyanoacrylate monomers are subjected to a polymerization reaction in an acidic medium comprising a first modifier; preferably, the acidic medium further comprises a stabilizer;

Step 2: a base is added to the reaction mixture of Step 1 until the reaction mixture is neutral, the reaction mixture is filtrated, and the filtrate is lyophilized;

Step 3: the lyophilized product is dispersed in a buffer, a second modifier is added, and incubation is performed; and Step 4: nanoparticles are separated from the mixture of Step 3; preferably, the separation includes filtration and/or lyophilization.

In one preferred embodiment, in Step 1, the n-butyl cyanoacrylate monomer and the acidic medium have a mass/volume ratio of 0.05%~1% g/ml, e.g. 0.05%~0.1% g/ml, 0.1%~0.5% g/ml, 0.1%~0.75% g/ml or 0.75%~1% g/ml.

In one preferred embodiment, in Step 1, the first modifier and the acidic medium have a mass/volume ratio of 0.5%~5% g/ml, e.g. 0.5%~1% g/ml, 0.5%~2% g/ml, 1%~3% g/ml or 3%~5% g/ml.

In one preferred embodiment, in Step 1, the stabilizer and the acidic medium have a mass/volume ratio of 0.05%~5% g/ml, e.g. 0.5%~1% g/ml, 0.5%~2% g/ml, 1%~3% g/ml or 3%~5% g/ml.

In one preferred embodiment, in Step 1, the stabilizer is selected from the group consisting of cyclodextrin (e.g. Dex70), polyvinyl pyrrolidone (e.g. PVP-K30) and poloxamer (e.g. Poloxamer F68).

In one preferred embodiment, the acidic medium is a hydrochloric acid solution; preferably, the hydrochloric acid solution has a pH of 1.0~3.0.

In one preferred embodiment, the polymerization reaction is carried out at room temperature.

In one preferred embodiment, the polymerization reaction in Step 1 is carried out for 1~10 h, e.g. 1~5 h, 2~6 h, 3~7 h, 4~8 h or 5~10 h.

In one preferred embodiment, in Step 2, the base is sodium hydroxide.

In one preferred embodiment, in Step 2, filtration is performed by using a filtration membrane, preferably, filtration is performed by using a filtration membrane with a pore size of 0.45 μm.

In one preferred embodiment, in Step 3, the buffer is a phosphate buffer.

In one preferred embodiment, in Step 3, the second modifier and the buffer have a mass/volume ratio of 0.05%~2% g/ml, e.g. 0.05%~0.1% g/ml, 0.1%~0.5% g/ml, 0.5%~1% g/ml or 1%~2%.

In one preferred embodiment, in Step 3, incubation is performed for 0.5~5 h, e.g. 0.5~1 h, 1~2 h, 2~3 h, 3~4 h or 4~5 h.

The nanoparticle according to the invention is modified with two modifiers on the surface, and optionally, the modifier molecules are tangled with the molecular chain of poly(n-butyl cyanoacrylate), and therefore are fixed on the nanoparticle surface; or adsorb on the nanoparticle surface via hydrogen bonds, intermolecular force or hydrophobic interaction; or are linked onto the nanoparticle surface via chemical bonds.

The nanoparticle according to the invention may be used to load a drug, so as to enhance the BBB permeability of the drug, and enable the sustained release of the drug.

The drug can be entrapped into the inner of the nanoparticle, or linked to the surface of the nanoparticle via chemical bonds. Preferably, the drug is entrapped into the inner of the nanoparticle, to ensure stable and effective delivery of the drug.

Therefore, in another aspect, the invention provides a drug delivery system, comprising the nanoparticle as described above, wherein the nanoparticle is loaded with a drug.

In one preferred embodiment, the drug is used for diagnosing, preventing and/or treating a central nervous system disease in a subject.

In one preferred embodiment, the drug is a paclitaxel drug (e.g. paclitaxel, docetaxel, cabazitaxel or larotaxel, preferably docetaxel).

In one preferred embodiment, the drug is a fluorescent substance (e.g. coumarin and a derivative thereof, e.g. coumarin-6).

In one preferred embodiment, the drug is encapsulated in the nanoparticle.

In one preferred embodiment, in the drug delivery system, the nanoparticle has a drug entrapment efficiency of 80%~100%, e.g. 80%~85%, 85%~90%, 90%~95% or 95%~100%.

In one preferred embodiment, the drug delivery system has a drug loading rate of 1%~10%, e.g. 1%~3%, 3%~5%, 5%~7% or 7%~10%.

In one preferred embodiment, the drug delivery system is prepared by a method comprising the following steps:

Step 1: n-butyl cyanoacrylate monomers are subjected to a polymerization reaction in an acidic medium comprising a first modifier; preferably, the acidic medium further comprises a stabilizer;

Step 2: a drug is added to the reaction mixture, and then the polymerization reaction is further performed;

Step 3: a base is added to the reaction mixture until the reaction mixture is neutral, the reaction mixture is filtrated, and the filtrate is lyophilized;

Step 4: the lyophilized product is dispersed in a buffer, a second modifier is added, and incubation is performed; and Step 5: nanoparticles are separated from the mixture of Step 4; preferably, the separation includes filtration and/or lyophilization.

In one preferred embodiment, in Step 1, the n-butyl cyanoacrylate monomer and the acidic medium have a mass/volume ratio of 0.05%~1% g/ml, e.g. 0.05%~0.1% g/ml, 0.1%~0.5% g/ml, 0.1%~0.75% g/ml or 0.75%~1% g/ml.

In one preferred embodiment, in Step 1, the first modifier and the acidic medium have a mass/volume ratio of 0.5%~5% g/ml, e.g. 0.5%~1% g/ml, 0.5%~2% g/ml, 1%~3% g/ml or 3%~5% g/ml.

In one preferred embodiment, in Step 1, the stabilizer and the acidic medium have a mass/volume ratio of 0.05%~5% g/ml, e.g. 0.5%~1% g/ml, 0.5%~2% g/ml, 1%~3% g/ml or 3%~5% g/ml.

In one preferred embodiment, in Step 1, the stabilizer is selected from the group consisting of cyclodextrin (e.g. Dex70), polyvinyl pyrrolidone (e.g. PVP-K30) and poloxamer (e.g. Poloxamer F68).

In one preferred embodiment, the acidic medium is a hydrochloric acid solution; preferably, the hydrochloric acid solution has a pH of 1.0~3.0.

In one preferred embodiment, the polymerization reaction is carried out at room temperature.

In one preferred embodiment, the polymerization reaction in Step 1 is carried out for 1~10 h, e.g. 1~5 h, 2~6 h, 3~7 h, 4~8 h or 5~10 h.

In one preferred embodiment, the drug and the cyanoacrylate monomer have a mass ratio of is 1~20:1, e.g. 1~5:1, 3~10:1, 5~15:1 or 15~20:1.

In one preferred embodiment, in Step 2, after the drug is added, the polymerization reaction is performed for 0.5~5 h, e.g. 0.5~1 h, 1~2 h, 2~3 h, 3~4 h or 4~5 h.

In one preferred embodiment, in Step 3, the base is sodium hydroxide.

In one preferred embodiment, in Step 3, filtration is performed by using a filtration membrane, preferably, filtration is performed by using a filtration membrane with a pore size of 0.45 μm.

In one preferred embodiment, in Step 4, the buffer is a phosphate buffer.

In one preferred embodiment, in Step 4, the second modifier and the buffer have a mass/volume ratio of 0.05%~2% g/ml, e.g. 0.05%~0.1% g/ml, 0.1%~0.5% g/ml, 0.5%~1% g/ml or 1%~2%.

In one preferred embodiment, in Step 4, incubation is performed for 0.5~5 h, e.g. 0.5~1 h, 1~2 h, 2~3 h, 3~4 h or 4~5 h.

In another aspect, the invention provides a method for preparing the drug delivery system as described above, comprising the following steps:

Step 1: n-butyl cyanoacrylate monomers are subjected to a polymerization reaction in an acidic medium comprising a first modifier; preferably, the acidic medium further comprises a stabilizer;

Step 2: a drug is added to the reaction mixture, and then the polymerization reaction is further performed;

Step 3: a base is added to the reaction mixture until the reaction mixture is neutral, the reaction mixture is filtrated, and the filtrate is lyophilized;

Step 4: the lyophilized product is dispersed in a buffer, a second modifier is added, and incubation is performed; and Step 5: nanoparticles are separated from the mixture of Step 4; preferably, the separation includes filtration and/or lyophilization.

In one preferred embodiment, in Step 1, the n-butyl cyanoacrylate monomer and the acidic medium have a mass/volume ratio of 0.05%~1% g/ml, e.g. 0.05%~0.1% g/ml, 0.1%~0.5% g/ml, 0.1%~0.75% g/ml or 0.75%~1% g/ml.

In one preferred embodiment, in Step 1, the first modifier and the acidic medium have a mass/volume ratio of 0.5%~5% g/ml, e.g. 0.5%~1% g/ml, 0.5%~2% g/ml, 1%~3% g/ml or 3%~5% g/ml.

In one preferred embodiment, in Step 1, the stabilizer and the acidic medium have a mass/volume ratio of 0.05%~5% g/ml, e.g. 0.5%~1% g/ml, 0.5%~2% g/ml, 1%~3% g/ml or 3%~5% g/ml.

In one preferred embodiment, in Step 1, the stabilizer is selected from the group consisting of cyclodextrin (e.g. Dex70), polyvinyl pyrrolidone (e.g. PVP-K30) and poloxamer (e.g. Poloxamer F68).

In one preferred embodiment, the acidic medium is a hydrochloric acid solution; preferably, the hydrochloric acid solution has a pH of 1.0~3.0.

In one preferred embodiment, the polymerization reaction is carried out at room temperature.

In one preferred embodiment, the polymerization reaction in Step 1 is carried out for 1~10 h, e.g. 1~5 h, 2~6 h, 3~7 h, 4~8 h or 5~10 h.

In one preferred embodiment, the ratio of the drug and the cyanoacrylate monomer by mass is 1~20:1, e.g. 1~5:1, 3~10:1, 5~15:1 or 15~20:1.

In one preferred embodiment, in Step 2, after the drug is added, the polymerization reaction is performed for 0.5~5 h, e.g. 0.5~1 h, 1~2 h, 2~3 h, 3~4 h or 4~5 h.

In one preferred embodiment, in Step 3, the base is sodium hydroxide.

In one preferred embodiment, in Step 3, filtration is performed by using a filtration membrane, preferably, filtration is performed by using a filtration membrane with a pore size of 0.45 μm.

In one preferred embodiment, in Step 4, the buffer is a phosphate buffer.

In one preferred embodiment, in Step 4, the second modifier and the buffer have a mass/volume ratio of 0.05%~2% g/ml, e.g. 0.05%~0.1% g/ml, 0.1%~0.5% g/ml, 0.5%~1% g/ml or 1%~2%.

In one preferred embodiment, in Step 4, incubation is performed for 0.5~5 h, e.g. 0.5~1 h, 1~2 h, 2~3 h, 3~4 h or 4~5 h.

In one aspect, the invention provides use of the nanoparticle as described above for manufacture of a drug delivery system comprising the nanoparticle loaded with a drug.

In one preferred embodiment, the drug is used for diagnosing, preventing and/or treating a central nervous system disease in a subject.

In one preferred embodiment, the drug is a paclitaxel drug (e.g. paclitaxel, docetaxel, cabazitaxel or larotaxel, preferably docetaxel).

In one preferred embodiment, the drug is a fluorescent substance (e.g. coumarin and a derivative thereof, e.g. coumarin-6).

In one preferred embodiment, the drug is encapsulated in the nanoparticle.

In one preferred embodiment, in the drug delivery system, the nanoparticle has a drug entrapment efficiency of 80%~100%, e.g. 80%~85%, 85%~90%, 90%~95% or 95%~100%.

In one preferred embodiment, the drug delivery system has a drug loading rate of 1%~10%, e.g. 1%~3%, 3%~5%, 5%~7% or 7%~10%.

In one aspect, the invention provides a pharmaceutical composition, comprising the drug delivery system as described above. Preferably, the pharmaceutical composition is used for diagnosing, preventing and/or treating a central nervous system disease in a subject.

In one aspect, the invention provides use of the nanoparticle or the drug delivery system as described above for manufacture of a pharmaceutical composition for diagnosing, preventing and/or treating a central nervous system disease in a subject.

In the invention, optionally, the pharmaceutical composition further comprises a pharmaceutically acceptable adjuvant (e.g. a carrier and/or an excipient). Preferably, the carrier and/or excipient is selected from the group consisting of an ion exchanger, aluminum oxide, aluminum stearate, lecithin, serum protein (e.g. human serum protein), glycerol, sorbic acid, potassium sorbate, a partial glyceride mixture of saturated plant fatty acid, water, protamine sulfate, disodium hydrogen phosphate, potassium hydrogen phosphate, sodium chloride, zinc salt, colloid silica, magnesium trisilicate, polyvinylpyrrolidone, cellulose substance, polyethylene glycol, carboxymethylcellulose sodium, polyacrylic ester, beewax, polyethylene-polyoxypropylene block copolymer, and lanolin.

In the invention, the pharmaceutical composition may be prepared in any pharmaceutically acceptable dosage form. For example, the pharmaceutical composition according to the invention may be prepared into a tablet, a capsule, a pill, a granule, a solution, a suspension, a syrup, an injection (including a liquid injection, a powder for injection or a tablet for injection), a suppository, an inhalant, or a spraying agent.

In addition, the pharmaceutical composition according to the invention may also be administered to a subject by any suitable route, such as orally, parenterally, rectally, intrapulmonarily or topically. In some preferred embodiments, the pharmaceutical composition is suitable for oral, parenteral (intravenous, intramuscular or subcutaneous), transdermal, translingual, or inhalation administration.

When administered orally, the pharmaceutical composition may be prepared into an oral formulation, e.g. an oral solid formulation such as a tablet, a capsule, a pill, and a granule; or an oral liquid formulation, such as an oral solution, an oral suspension, and a syrup. When being prepared into an oral formulation, the pharmaceutical composition may also comprise a suitable filler, binding agent, disintegrating agent, or lubricant, etc. When administered parenterally, the pharmaceutical composition may be prepared into an injection, including a liquid injection, a powder for injection or a tablet for injection. When being prepared into an injection, the pharmaceutical composition may be prepared by a conventional method existing in the pharmaceutical field. When an injection is prepared, to the pharmaceutical composition, no additive may be added, or a suitable additive may be added depending on the property of drug. When administered rectally, the pharmaceutical composition may be prepared into a suppository, etc. When administered intrapulmonarily, the pharmaceutical composition may be prepared into an inhalant, or a spraying agent, etc.

In some preferred embodiments, the nanoparticle or the drug delivery system according to the invention is present in the form of a unit dose in a pharmaceutical composition or a medicament.

In some preferred embodiments, an effective amount of the pharmaceutical composition is administered to a subject. As used herein, the term "an effective amount" refers to an amount that is sufficient to achieve or at least partially achieve a desired effect. For example, an effective amount for preventing a disease (e.g. a central nervous system disease) refers to an amount that is sufficient to prevent, suppress or delay the development of a disease (e.g. a central nervous system disease); an effective amount for treating a disease refers to an amount that is sufficient to cure or at least partially suppress a disease and its complication in a patient with the disease. The determination of such an effective amount is completely within the ability of a person skilled in the art. For example, an amount effective for a therapeutic use depends on the severity of a disease to be treated, general state of the immune system in a patient, general conditions of a patient, such as age, body weight and gender, administration means of drugs, additional therapies used simultaneously, and the like.

In one aspect, the invention provides a method for diagnosing, preventing and/or treating a central nervous system disease in a subject, comprising administering to the subject the drug delivery system or the pharmaceutical composition as described above.

In one aspect, the invention provides a method for enhancing the ability of a drug to penetrate across the blood brain barrier in a subject, comprising loading the nanoparticle as described above with the drug. Preferably, the drug is used for diagnosing, preventing and/or treating a central nervous system disease in a subject.

In one aspect, the invention provides a method for promoting drug penetration across the blood brain barrier in a subject, comprising loading the nanoparticle as described above with a drug, and administering the drug to the subject. Preferably, the drug is used for diagnosing, preventing and/or treating a central nervous system disease in a subject.

For example, in the Examples of the invention, when a nanoparticle with dual modifications is loaded with a drug, it can enhance the ability of the drug to penetrate across the blood brain barrier in a rat, so as to enhance the content of a drug in the brain tissue of a rat.

In one aspect, the invention provides the use of the nanoparticle as described above, for enhancing the ability of a drug to penetrate across the blood brain barrier in a subject. Preferably, the drug is used for diagnosing, preventing and/or treating a central nervous system disease in a subject.

In one aspect, the invention provides the use of the nanoparticle as described above, for promoting drug penetration across the blood brain barrier in a subject. Preferably, the drug is used for diagnosing, preventing and/or treating a central nervous system disease in a subject.

In one aspect, the invention provides the nanoparticle as described above, which is used to enhance the ability of a drug to penetrate across the blood brain barrier in a subject. Preferably, the drug is used for diagnosing, preventing and/or treating a central nervous system disease in a subject.

In one aspect, the invention provides the nanoparticle as described above, which is used to promote drug penetration across the blood brain barrier in a subject. Preferably, the drug is used for diagnosing, preventing and/or treating a central nervous system disease in a subject.

In one aspect, the invention provides the drug delivery system as described above, which is used for diagnosing, preventing and/or treating a central nervous system disease in a subject.

In the invention, preferably, the central nervous system disease is selected from the group consisting of brain tumor, cerebral stroke, epilepsy, Alzheimer's disease, Parkinson's disease, Huntington's disease, amyotrophic lateral sclerosis, demyelinating disease, multiple sclerosis, schizophrenia, depression and central nervous system damage.

In the invention, preferably, the subject is a mammal, such as a bovine, an equine, a caprid, a suidae, a canine, a feline, a rodent, or a primate; e.g. a human.

Beneficial Effects

The invention provides a PBCA nanoparticle with dual modifications, which is safer and more effective than PBCA nanoparticles modified with a surfactant such as Tween-80. The nanoparticle according to the invention can penetrate across the BBB to arrive at the brain, has a good BBB permeability and is effectively accumulated in the brain tissue.

When the nanoparticle according to the invention is loaded with a drug, it can effectively enhance the intracerebral concentration and the brain-targeting property of the drug, and enable the drug to have a good sustained-release property, so as to achieve stable and long-term release of the drug in vivo. The nanoparticle and the drug delivery system according to the invention can enhance the BBB permeability of a drug, and promote the entry of the drug into the brain, and therefore are more favorable for the diagnosis, prevention and/or treatment of a central nervous system disease.

The embodiments of the invention are illustrated in detail by reference to the following drawings and examples. However, it is understood by those skilled in the art that the following drawings and examples are used only for the purpose of illustrating the invention, rather than limiting the protection scope of the invention. According to the detailed description of the following drawings and preferred embodiments, various purposes and advantages of the invention are obvious for those skilled in the art.

DESCRIPTION OF THE DRAWINGS

FIG. 3 shows the result of the structural characterization of coumarin-6-loaded PBCA nanoparticles with dual modifications by $PEG_{20000}$-cholesterol in Example 2, wherein, FIGS. 3(A)-3(C) show the DSC thermograms of $mPEG_{20000}$, cholesterol and coumarin-6. As seen from the figure, $mPEG_{20000}$, cholesterol and coumarin-6 had a melting peak at 68.21° C., 149.98° C. and 208.29° C., respectively. FIG. 3(D) shows the DSC thermogram of coumarin-6-loaded PBCA nanoparticles with dual modifications by $PEG_{20000}$-cholesterol. In the figure, the melting peaks of $mPEG_{20000}$ and cholesterol were still present, indicating that $PEG_{20000}$ and cholesterol were not entrapped in the inner of the nanoparticles, and instead, were involved in the modification of nanoparticles on the surface; the melting peak of coumarin-6 disappeared, indicating that coumarin-6 was encapsulated into a nanoparticle.

FIG. 4 (B) shows the comparison of the in vitro release curves of common nanoparticles loaded with coumarin-6, coumarin-6-loaded nanoparticles with single modification by $PEG_{20000}$, and coumarin-6-loaded nanoparticles with dual modifications by $PEG_{20000}$-cholesterol in Example 4 (n=6). As shown in the figure, as compared with the unmodified nanoparticles and the nanoparticles with single modification by $PEG_{20000}$, the nanoparticles with dual modifications by $PEG_{20000}$-cholesterol had a more significant sustained-release property.

FIG. 6 (B) shows the content of coumarin-6 in the brain tissue of the rats injected with different samples in Example 6, wherein the samples from left to right were a free drug solution, common nanoparticles, PBCA nanoparticles with single modification by $PEG_{20000}$, and PBCA nanoparticles with dual modifications by $PEG_{20000}$-cholesterol, respectively. In the figure, \*\*: $p<0.05$ VS a free drug solution group; ##: $p<0.05$ VS a common nanoparticle group; &&: $p<0.05$ VS a group of nanoparticles with single modification by PEG. As shown in the figure, the PBCA nanoparticles with single modification by $PEG_{20000}$ had a significantly increased content of coumarin-6 in the brain tissue, as compared with the free drug solution and the common PBCA nanoparticles ($P<0.01$). The PBCA nanoparticles with dual modifications by $PEG_{20000}$-cholesterol according to the invention had a significantly increased content of coumarin-6 in the brain tissue, as compared with the PBCA nanoparticles with single modification by $PEG_{20000}$ ($P<0.01$). The result showed that the PBCA nanoparticles with dual modifications by $PEG_{20000}$-cholesterol had good BBB permeability, and could significantly promote the passage of drug through blood-brain barrier.

SPECIFIC MODES FOR CARRYING OUT THE INVENTION

Figure 1:
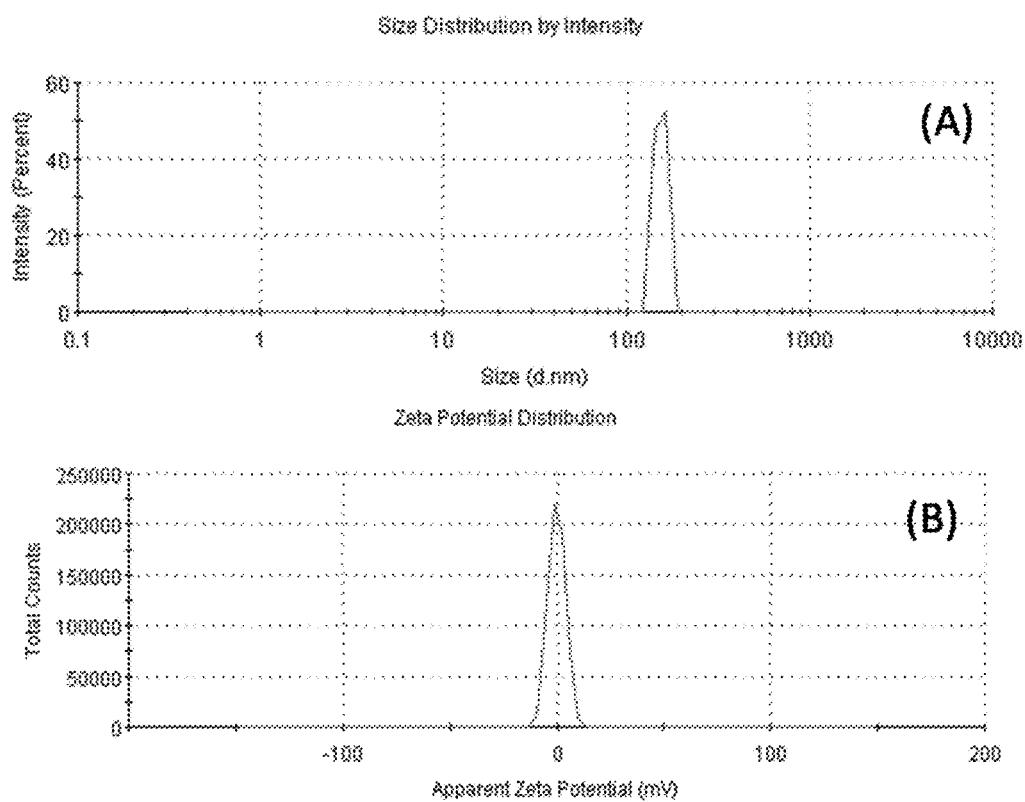
FIG. 1 shows the result of the measurement for particle size (A) and Zeta potential (B) of coumarin-6-loaded PBCA nanoparticles with dual modifications by $PEG_{20000}$-cholesterol in Example 1. As seen from the figure, the nanoparticle had a narrow particle size distribution, an average particle size of 185.4 nm, and a Zeta potential of −0.66 mV.

The embodiments of the invention are illustrated in detail by reference to the following examples. However, it is understood by those skilled in the art that the examples are used only for the purpose of illustrating the invention, rather than limiting the protection scope of the invention. In the case where the concrete conditions are not indicated in the examples, the examples are carried out according to conventional conditions or the conditions recommended by the manufacturer. The agents or instruments of which the manufacturer are not indicated are regular products that can be purchased on the market.

Example 1. Preparation and Evaluation of Coumarin-6-Loaded PBCA Nanoparticles with Dual Modifications by $PEG_{20000}$-Cholesterol (1) Method for preparing coumarin-6-loaded PBCA nanoparticles with dual modifications by $PEG_{20000}$-cholesterol: the stabilizer Dex70 (1%, w/v) and methoxypolyethylene glycol having a number-average molecular weight of 20000 ($mPEG_{20000}$) (1.5%, w/v) were dissolved in a HCl medium (pH 1.0), and BCA monomers (1%, v/v) were slowly added dropwise at room temperature under magnetic stirring. After stirring at 500 rpm for 4 h, coumarin-6 (1%, w/v) was added, and the stirring was performed at 750 rpm for 2.5 h. Then, the system was neutralized with NaOH to pH of 6-7, and was further stirred for 1 h so that BCA monomers were sufficiently polymerized, thereby obtaining PEG-PBCA nanoparticles.

After filtration through a filtration membrane (0.45 μm), the PEG-PBCA nanoparticles obtained were lyophilized, and then were re-dissolved in PBS, and mixed homogeneously for 30 min. Cholesterol (1%, w/v) was added, and incubation was performed for 0.5 h. The resultant mixture was filtrated, and centrifuged at 20000 rpm for 30 min. The supernatant was removed, and the precipitate was re-suspended in a suitable amount of double distilled water, and then lyophilized, thereby obtaining coumarin-6-loaded PBCA nanoparticles with dual modifications by $PEG_{20000}$-cholesterol, which were stored in a drier.

Method for preparing coumarin-6-loaded PBCA nanoparticles with single modification by $PEG_{20000}$: the stabilizer Dex70 (1%, w/v) and $mPEG_{20000}$ (1.5%, w/v) were dissolved in a HCl medium (pH 1.0), and then BCA monomers (1%, v/v) were slowly added dropwise at room temperature under magnetic stirring. After stirring at 500 rpm for 4 h, coumarin-6 (1%, w/v) was added, and the stirring was performed at 750 rpm for 2.5 h. Then, the system was neutralized with NaOH to pH of 6-7, and was further stirred for 1 h so that BCA monomers were sufficiently polymerized, thereby obtaining coumarin-6-loaded PBCA nanoparticles with single modification by $PEG_{200000}$. After filtration through a filtration membrane (0.45 μm), the nanoparticles obtained were lyophilized, which were stored in a drier, as an experimental control.

By the method above, common unmodified PBCA nanoparticles comprising coumarin-6, and coumarin-6-loaded nanoparticles with single modification by cholesterol, were also prepared, as control.

(2) Measurement and Result of particle size and potential: coumarin-6-loaded PBCA nanoparticles with dual modifications by $PEG_{20000}$-cholesterol were diluted with deionized water to a suitable concentration, and ultrasonically treated for 30 min, so as to mix the solution sufficiently. After filtration through a microfiltration membrane (0.45 μm), the filtrate was measured for particle size and potential at 25° C., and the result was shown in FIG. 1. FIG. 1 (A) showed the measurement result of the particle size of nanoparticles, and FIG. 1 (B) showed the measurement result of the Zeta potential of nanoparticles. As seen from the figure, the coumarin-6-loaded PBCA nanoparticles with dual modifications by $PEG_{20000}$-cholesterol had a narrow particle size distribution, an average particle size of 185.4 nm, a PDI of 0.133, and a Zeta potential of −0.66 mV.

By the method above, coumarin-6-loaded PBCA nanoparticles with single modification by $PEG_{20000}$ were measured for particle size and Zeta potential, which had an average particle size of 194.3 nm, a PDI of 0.159, and a Zeta potential of −8.04 mV.

(3) Measurement and Result of entrapment efficiency and drug loading rate: a suspension (200 μl) of coumarin-6-loaded PBCA nanoparticles with dual modifications by $PEG_{20000}$-cholesterol was added in a Vivaspin ultrafiltration centrifuge tube (MWCO: 2000, Sartorius company, Germany) and centrifuged at 4000 rpm for 20 min, and the free-form drug, which was not encapsulated into nanoparticles, was separated into the lower layer of the ultrafiltration centrifuge tube. The concentration of coumarin-6 in the lower layer was determined by Fluorescence/Chemiluminescence Analyzer, and the entrapment efficiency was calculated.

To a suspension of coumarin-6-loaded PBCA nanoparticles with dual modifications by $PEG_{20000}$-cholesterol (20 μl), acetonitrile (1980 μl) was added, and the nanoparticle structure was destructed by shaking for 30 s, so as to release the drug. The concentration of coumarin-6 was determined by Fluorescence/Chemiluminescence Analyzer, and the drug loading rate was calculated.

Result: coumarin-6-loaded PBCA nanoparticles with dual modifications by $PEG_{20000}$-cholesterol had an entrapment efficiency of 97.8%, and a drug loading rate of 2.07%.

By the method above, the entrapment efficiency and the drug loading rate of coumarin-6-loaded PBCA nanoparticles with single modification by $PEG_{20000}$ were determined, which were 98.6% and 2.03%, respectively.

Example 2. Morphological and Structural Characterization of Coumarin-6-Loaded PBCA Nanoparticles with Dual Modifications by $PEG_{20000}$-Cholesterol (1) Morphological Characterization Method: Transmission Electron Microscope (TEM) was used for morphological characterization of coumarin-6-loaded PBCA nanoparticles with single modification by cholesterol and coumarin-6-loaded PBCA nanoparticles with dual modifications by $PEG_{20000}$-cholesterol. A given amount of lyophilized nanoparticles was weighed, and diluted with pure water until the nanoparticles had a concentration of 0.5 mg/ml. The resultant solution was mixed homogenously by shaking for 100 times, 5 μl solution was pipetted and added dropwise to a Formvar-coated copper grid, and a drop of 1% (w/v) phosphotungstic acid aqueous solution was added for staining when the grid was almost dry. After staining for 2 min, most of the liquid was pipetted off carefully, and only a liquid film was left. After the liquid film was completely dried, it was observed by TEM.

Figure 2:
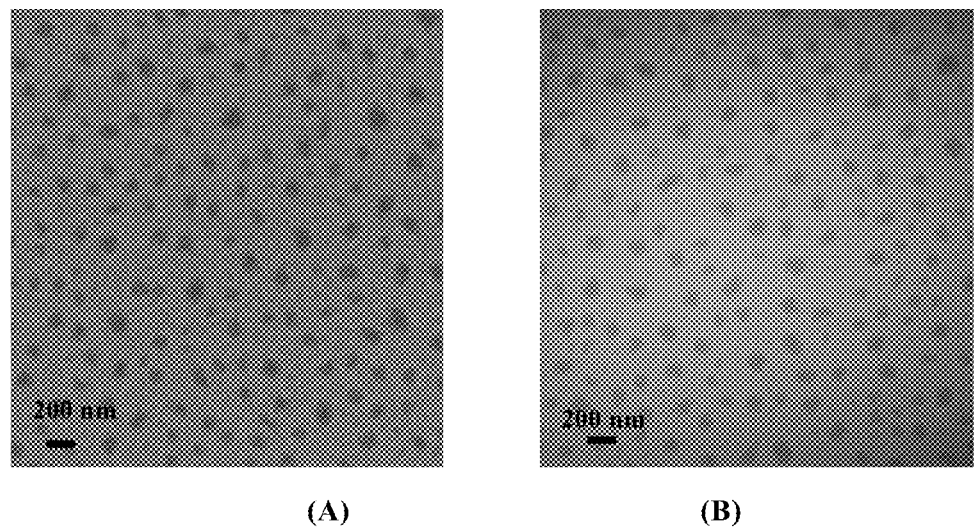
FIG. 2 shows the TEM photographs of coumarin-6-loaded PBCA nanoparticles with single modification by cholesterol (FIG. 2 (A)) and coumarin-6-loaded PBCA nanoparticles with dual modifications by $PEG_{20000}$-cholesterol (FIG. 2 (B)) in Example 2. As seen from the figures, for both PBCA nanoparticles with single modification by cholesterol and PBCA nanoparticles with dual modifications by $PEG_{20000}$-cholesterol, the nanoparticles were uniform in size, had a particle size of about 200 nm, and had good dispersion and no phenomenon of large-scale aggregation, and the two nanoparticles had little difference in morphology, indicating that dual modifications by $PEG_{20000}$-cholesterol had little effect on the morphology of nanoparticles.

Result: the TEM photographs of the two samples were shown in FIG. 2. FIGS. 2(A) and (B) showed the TEM photographs of coumarin-6-loaded PBCA nanoparticles with single modification by cholesterol and coumarin-6-loaded PBCA nanoparticles with dual modifications by $PEG_{20000}$-cholesterol. As seen from the figure, for both PBCA nanoparticles with single modification by cholesterol and PBCA nanoparticles with dual modifications by $PEG_{20000}$-cholesterol, the nanoparticles were uniform in size, had a particle size of about 200 nm, had good dispersion and no phenomenon of large-scale aggregation, and the two nanoparticles had little difference in morphology, indicating dual modifications by $PEG_{20000}$-cholesterol had little effect on the morphology of nanoparticles.

(2) Structural Characterization

Method: Differential Scanning Calorimetry (DSC) was used for structural characterization of coumarin-6-loaded PBCA nanoparticles with dual modifications by $PEG_{20000}$-cholesterol. Coumarin-6 (about 5 mg), $mPEG_{20000}$ (about 5 mg), cholesterol (about 5 mg) and coumarin-6-loaded PBCA nanoparticles with dual modifications by $PEG_{20000}$-cholesterol (about 5 mg) were separately weighed, and placed in T zero aluminum trays (Waters company, USA), each of which was covered with a lid to seal. The reference tray was a blank T zero aluminum tray. The temperature was decreased to 0° C., kept at 0° C. for 5 min, and then increased at a rate of 10° C./min.

Figure 3:
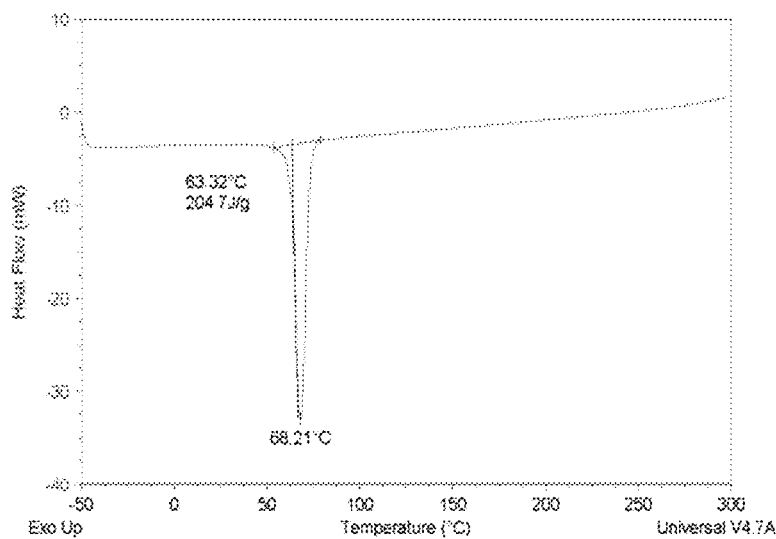
Figure 3:
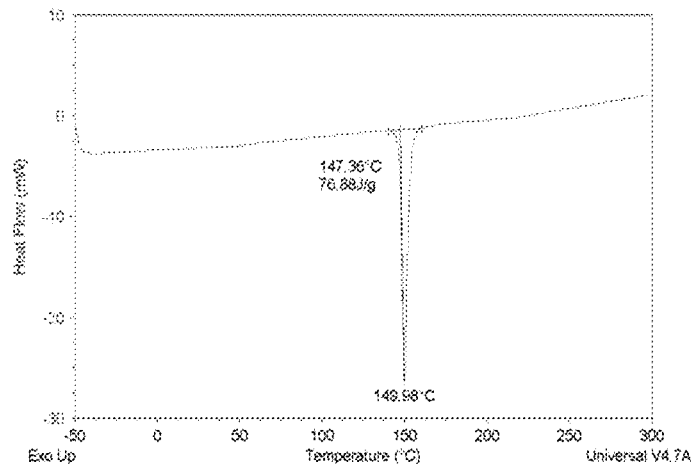
Figure 3:
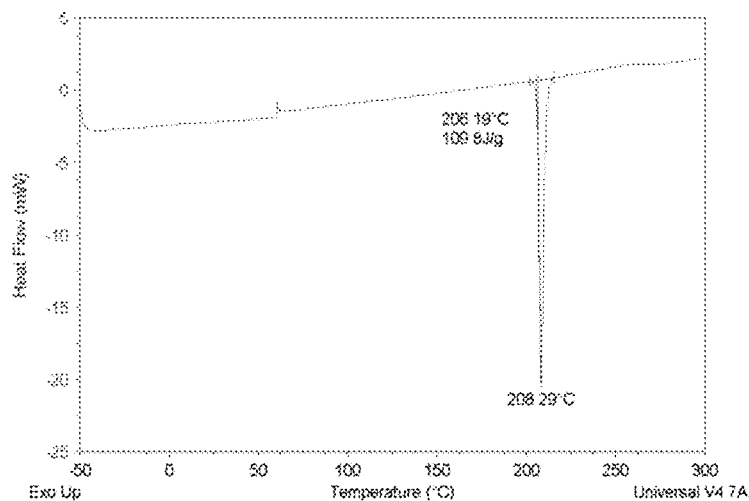
Figure 3:
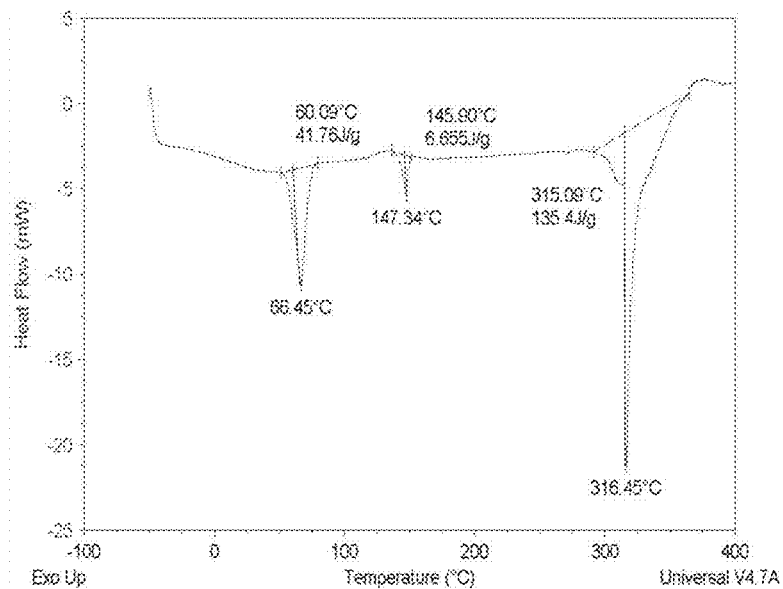

Result: the DSC thermograms of the above four samples were shown in FIG. 3.

FIGS. 3(A)-(C) showed the DSC thermograms of $mPEG_{20000}$, cholesterol and coumarin-6. As seen from the figure, $mPEG_{20000}$, cholesterol and coumarin-6 had a melting peak at 68.21° C., 149.98° C. and 208.29° C., respectively.

FIG. 3(D) showed the DSC thermogram of coumarin-6-loaded PBCA nanoparticles with dual modifications by $PEG_{20000}$-cholesterol. In the figure, the melting peaks of $mPEG_{20000}$ and cholesterol were still present, indicating that $PEG_{20000}$ and cholesterol were not entrapped into nanoparticles, and instead were involved in the modification of nanoparticles on the surface; the melting peak of coumarin-6 disappeared, indicating that coumarin-6 was encapsulated into a nanoparticle. In addition, it could be seen from the figure that poly(n-butyl cyanoacrylate) was crosslinked from about 300° C., and had a significant endothermic peak at 316.45° C.

Example 3 Determination of the Cholesterol Concentration on the Surface of Coumarin-6-Loaded PBCA Nanoparticles with Dual Modifications by $PEG_{20000}$-Cholesterol (1) Method: Cholesterol Quantification Kit (Sigma-Aldrich, St. Louis, Mo., USA)) was used to determine the mass of cholesterol on the nanoparticle surface. The average number (N) of nanoparticles was calculated by the following formula (Olivier et al., 2002):

$$N = \frac{6 \times W \times 10^{-3}}{\pi \times (D \times 10^{-7})^3 \times \rho}$$

wherein, W represents the mass of nanoparticles, D represents the number of nanoparticles calculated by the average particle size of nanoparticles, and p represents density, i.e. the mass of nanoparticles in a unit volume, which is 1.1 g/cm³.

The cholesterol concentration on the nanoparticle surface was calculated by the following formula:

the cholesterol concentration on the nanoparticle surface=the mass of cholesterol on the nanoparticle surface/the average number of nanoparticles.

(2) Result: as calculated, the cholesterol concentration was $(8.5\pm0.4)\times10^7$ ng/nanoparticle on the surface of coumarin-6-loaded PBCA nanoparticles with dual modifications by $PEG_{20000}$-cholesterol.

Example 4. Study on the In Vitro Release of Coumarin-6-Loaded PBCA Nanoparticles with Dual Modifications by $PEG_{20000}$-Cholesterol (1) Method: a suspension (1 ml) of coumarin-6-loaded PBCA nanoparticles with dual modifications by $PEG_{20000}$-cholesterol was placed in a dialysis bag (MWCO: 20000, USA), and the dialysis bag was placed in 200 ml pH7.4 phosphate-buffered saline (PBS), under stirring at 100 rpm in dark in a 37° C. thermostatic water bath. The release medium (200 μl) was taken at different time points, and meanwhile PBS was supplemented. The concentration of coumarin-6 in the release medium was determined by Fluorescence/Chemiluminescence Analyzer, with blank PBS used as control, and for each time point, 6 samples were determined in parallel. By the same method, the in vitro release curves were determined for common nanoparticles loaded with coumarin-6, nanoparticles with single modification by cholesterol and PBCA nanoparticles with single modification by $PEG_{20000}$, as control. (2) Result: the release curves for the samples were shown in FIGS. 4 (A) and 4 (B).

Figure 4:
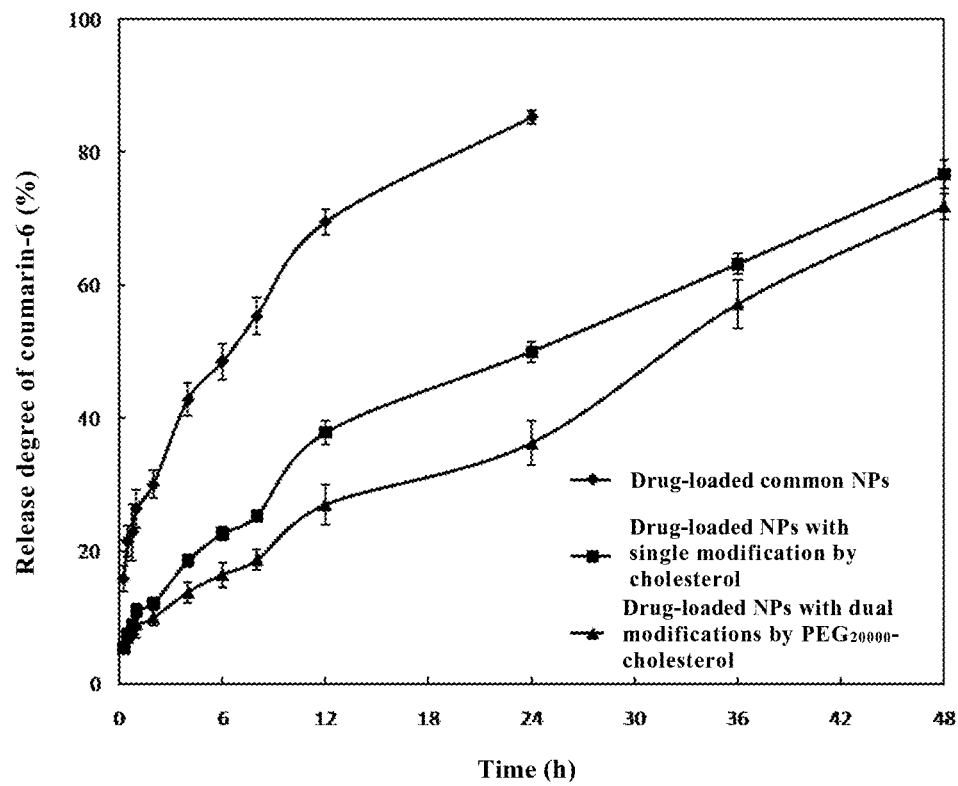
FIG. 4 (A) shows the comparison of the in vitro release curves of common nanoparticles loaded with coumarin-6, coumarin-6-loaded nanoparticles with single modification by cholesterol and coumarin-6-loaded PBCA nanoparticles with dual modifications by $PEG_{20000}$-cholesterol in Example 4 (n=6, n is the number of times for parallel tests, and n below has the same meanings). As shown in the figure, as compared with the common nanoparticles and the nanoparticles with single modification by cholesterol, the nanoparticles with dual modifications by $PEG_{20000}$-cholesterol had a significant sustained-release property and an improved release stability.
Figure 4:
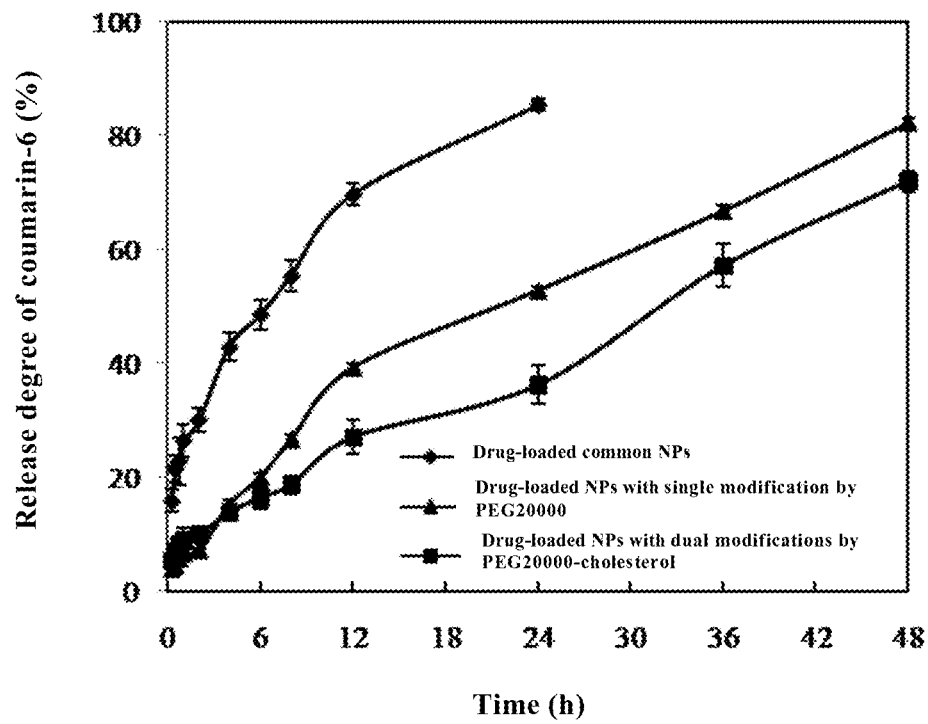

FIG. 4 (A) showed the comparison of in vitro release behavior of common nanoparticles loaded with coumarin-6, nanoparticles with single modification by cholesterol and nanoparticles with dual modifications by $PEG_{20000}$-cholesterol. As seen from the figure, the nanoparticles with dual modifications by $PEG_{20000}$-cholesterol were significantly different from the common nanoparticles in terms of in vitro release behavior ($f_2$=25.89, <50)

($f_2$ equation is a common criterion for evaluating the release behavior of two formulations, and its formula is as follows:

$$f_2 = 50 \log \left\{ \left[ 1 + \frac{1}{n} \sum_{t=1}^{n} (R_t - T_t)^2 \right]^{-0.5} \times 100 \right\}$$

wherein, $R_t$ represents the release degree of a reference sample at t time; $T_t$ represents the release degree of a test sample at t time; and n is the number of sampling points.

As prescribed by FDA, when $f_2$ is between 50 and 100, it is believed that the two formulations are not different in terms of drug release behavior under the same drug release conditions, and when $f_2$ is less than 50, it is believed that the two are significantly different.)

The common nanoparticles had the release finished within 24 h, and exhibited a high release degree in a short time. The nanoparticles with dual modifications by $PEG_{20000}$-cholesterol had a release time of above 48 h, and no burst release occurred in a short time. On one hand, it indicated that coumarin-6 was substantively encapsulated into nanoparticles with dual modifications, and on the other hand, it indicated that nanoparticles with dual modifications had a significant sustained-release property. As compared with the nanoparticles with single modification by cholesterol, the nanoparticles with dual modifications by $PEG_{20000}$-cholesterol had a lower release degree within the same period, indicating a more stable release behavior in vitro.

The result showed that as compared with the unmodified common nanoparticles or the nanoparticles with single modification by cholesterol, the nanoparticles with dual modifications by $PEG_{20000}$-cholesterol had a significant sustained-release property and a better release stability.

FIG. 4 (B) showed the comparison of the in vitro release behavior of common nanoparticles, nanoparticles with single modification by $PEG_{20000}$ and nanoparticles with dual modifications by $PEG_{20000}$-cholesterol, all of which were loaded with coumarin-6. As seen from the figure, in terms of in vitro release behavior, the nanoparticles with single modification by $PEG_{20000}$ were significantly different from the common nanoparticles ($f_2$=29.69, <50), and were not significantly different from the nanoparticles with dual modifications by $PEG_{20000}$-cholesterol ($f_2$=73.93, >50); however, 12 h later, the nanoparticles with dual modification had a better sustained-release property in vitro. The result showed that as compared with the unmodified nanoparticles and the nanoparticles with single modification by $PEG_{20000}$, the nanoparticles with dual modifications by $PEG_{20000}$-cholesterol had a more significant sustained-release property.

Example 5. Study on the Pharmacokinetics of Coumarin-6-Loaded PBCA Nanoparticles with Dual Modifications by $PEG_{20000}$-Cholesterol (1) Experimental purpose: to study the sustained-release property of coumarin-6-loaded PBCA nanoparticles with dual modifications by $PEG_{20000}$-cholesterol in animal.

(2) Method: 6- to 8-week old male Wistar rats were randomly divided into 3 groups, with 6 rats for each group. The rats were anesthetized by intraperitoneal injection of a pentobarbital solution (40 mg/kg), and jugular vein catheterization was performed. The rats were recovered for at least 12 h after the operation, and were subjected to tail vein injection with an equimolar amount of a coumarin-6 solution (a free drug), coumarin-6-loaded nanoparticles with single modification by cholesterol and PBCA nanoparticles with dual modifications by $PEG_{20000}$-cholesterol as prepared in Example 1, respectively. At different time points (5 min, 15 min, 30 min, 45 min, 1 h, 2 h, 4 h, 8 h, 12 h) after administration, blood (200 μl) was collected at the site where jugular vein catheterization was performed. After treatment, the content of coumarin-6 in the blood was determined.

Figure 5:
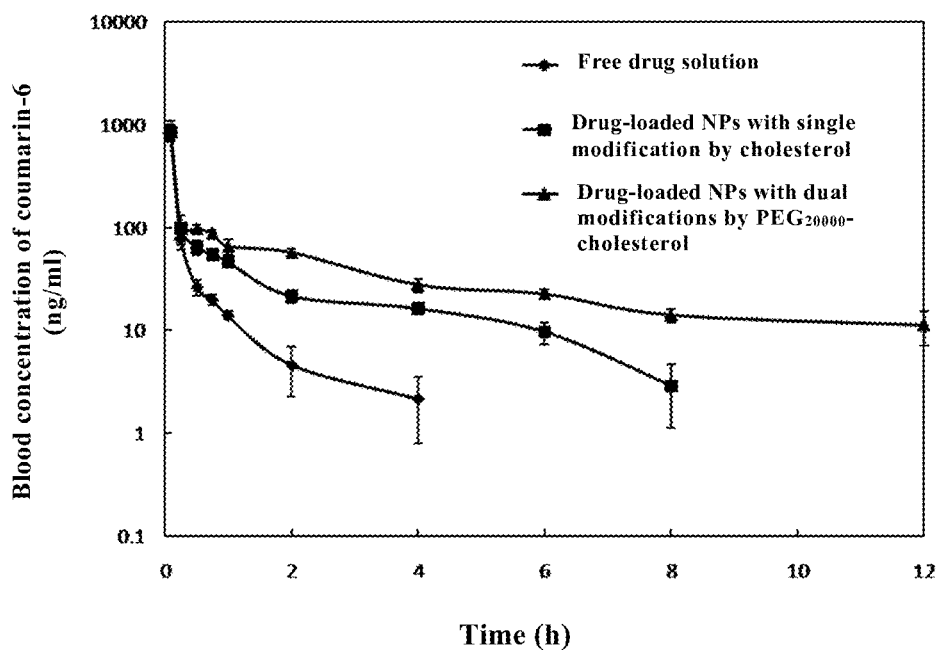
FIG. 5 shows the blood concentration—time curves of a coumarin-6 solution (a free drug), coumarin-6-loaded nanoparticles with single modification by cholesterol and coumarin-6-loaded PBCA nanoparticles with dual modifications by $PEG_{20000}$-cholesterol in Example 5 (n=6). As shown in the figure, the PBCA nanoparticles with dual modifications by $PEG_{20000}$-cholesterol could be released in vivo for a period of 12 h, and had a longer release time, and had a higher blood concentration at the same time, as compared with the free drug solution and the nanoparticles with single modification by cholesterol.

(3) Result: FIG. 5 showed the blood concentration—time curves of various samples. In the figure, the ordinate represents the concentration of coumarin-6 in blood, and the abscissa represents the time. As seen from the figure, different samples had significantly different blood concentration—time curves. After the administration of the free drug solution, the drug could be detected in blood only within 4 h, the release time was short, and there was no sustained-release effect; after administration of the nanoparticles with single modification by cholesterol, the release time was 8 h, longer than that of the free drug solution; the PBCA nanoparticles with dual modifications by $PEG_{20000}$-cholesterol (CLS-PEG NPs) could sustain the release for 12 h in vivo, and had a longer release time and a higher blood concentration as compared with the free drug solution and the nanoparticles with single modification by cholesterol (CLS NPs). The pharmacokinetic parameters were shown in Table 1.

TABLE 1

| | Coumarin-6 | | |
|---|---|---|---|
| Parameter | Free drug | CLS NPs | CLS-PEG NPs |
| $C_0$ (ng/ml) | 828.4 ± 139.0 | 853.5 ± 143.8 | 906.6 ± 175.5 |
| $t_{1/2}, \lambda_z$ (min) | 60.1 ± 24.0 | 106.8 ± 21.7** | 275.6 ± 117.4** |
| $AUC_{0-t}$ (μg · min/ml) | 15.8 ± 2.4 | 22.9 ± 3.0** | 35.2 ± 4.4** |
| $AUC_{0-\infty}$ (μg · min/ml) | 16.0 ± 2.3 | 23.3 ± 3.2** | 39.9 ± 5.3** |
| $V_d, \lambda_z$ (l) | 0.6 ± 0.3 | 0.6 ± 0.1 | 1.0 ± 0.4* |
| CL (ml/min) | 6.4 ± 0.9 | 4.4 ± 0.6** | 2.5 ± 0.4** |
| F (%) | — | 144.9 | 212.5 |

*p < 0.05,
**p < 0.01 vs. free-form drug group

The result showed that as compared with the free drug solution and the nanoparticles with single modification by cholesterol, the nanoparticles with dual modifications by $PEG_{20000}$-cholesterol had a significantly longer release time, a higher blood concentration, a better release behavior and a higher bioavailability in animal.

Example 6. Study on the Brain Tissue Distribution of Coumarin-6-Loaded PBCA Nanoparticles with Dual Modifications by $PEG_{20000}$-Cholesterol Research objective: to study the brain-targeting property of PBCA nanoparticles with dual modifications by $PEG_{20000}$-cholesterol in animal.

Experiment 1

(1) Method: 6- to 8-week old male Wistar rats were randomly divided into 3 groups, with 21 rats for each group. The rats were subjected to tail vein injection with an equimolar amount of a coumarin-6 solution (a free drug), coumarin-6-loaded nanoparticles with single modification by cholesterol and PBCA nanoparticles with dual modifications by $PEG_{20000}$-cholesterol as prepared in Example 1, respectively. The rats were killed at different time points (15 min, 30 min, 1 h, 2 h, 4 h, 8 h, 12 h) after administration, brain tissues were taken, and the content of coumarin-6 in brain was determined.

Figure 6:
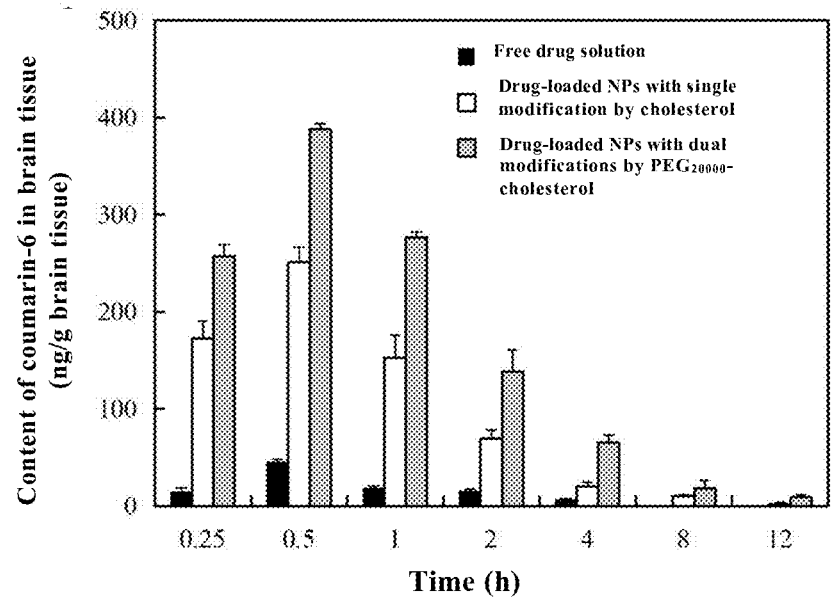
FIG. 6 (A) shows the content of coumarin-6 in the brain tissue at different time points after the rats were intravenously injected with a coumarin-6 solution (a free drug), coumarin-6-loaded nanoparticles with single modification by cholesterol, and coumarin-6-loaded PBCA nanoparticles with dual modifications by $PEG_{20000}$-cholesterol in Example 6, respectively (n=3). In the figure, for the nanoparticles with dual modifications by $PEG_{20000}$-cholesterol, P was less than 0.01, as compared with the free drug solution and the nanoparticles with single modification by cholesterol. As shown in the figure, the coumarin-6-loaded nanoparticles with dual modifications by $PEG_{20000}$-cholesterol could significantly enhance the content of coumarin-6 in the brain tissue of rats (which was significantly higher than that in the brain tissue of rats injected with a coumarin-6 solution (a free drug) and that in the brain tissue of rats injected with coumarin-6-loaded nanoparticles with single modification by cholesterol), and exhibited a sustained-release process.
Figure 6:
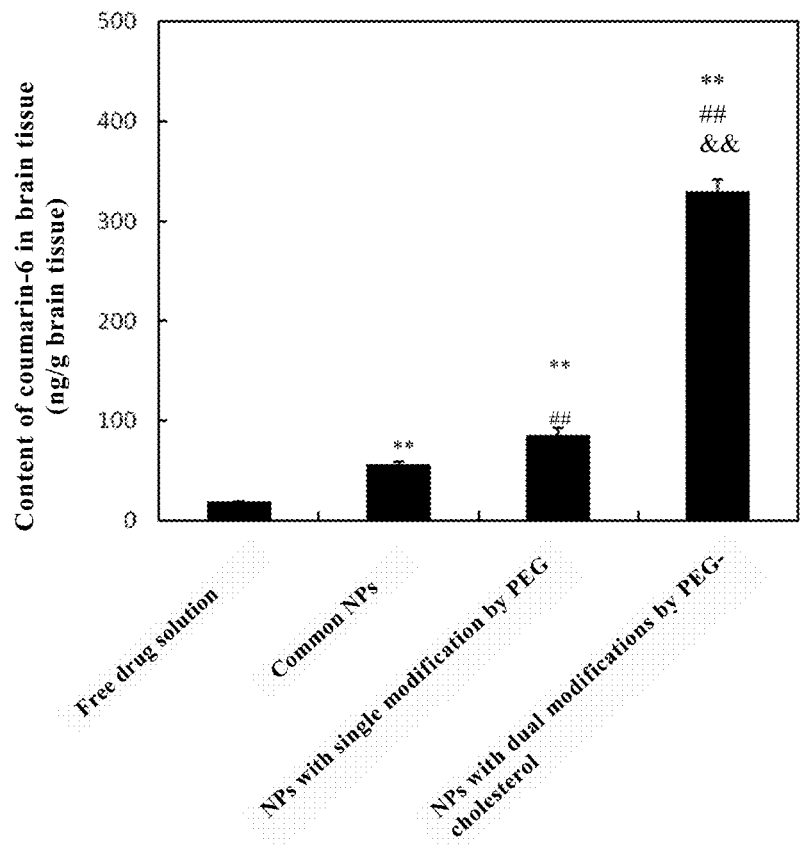

(2) Result: FIG. 6 (A) showed the concentration of coumarin-6 at different time points in the brain tissues of rats from different groups. As seen from the figure, the rats injected with the free drug solution had a low content of coumarin-6 in the brain tissue, which did not exceed 50 ng/g brain tissue, and no coumarin-6 was detected in the brain tissue 8 h after administration, indicating that free coumarin-6 had a low BBB permeability, and did not have a sustained-release property. The rats injected with coumarin-6-loaded nanoparticles with single modification by cholesterol had a much higher content of coumarin-6 in the brain tissue than that of the rats injected with free coumarin-6, however, no coumarin-6 was detected in the brain 8 h after administration. The rats injected with coumarin-6-loaded nanoparticles with dual modifications by $PEG_{20000}$-cholesterol had the content of coumarin-6 in the brain tissue further enhanced, as compared with the rats injected with nanoparticles with single modification by cholesterol, and coumarin-6 could be still detected in the brain 12 h after administration.

The result showed that as compared with free coumarin-6 and the coumarin-6-loaded nanoparticles with single modification by cholesterol, the coumarin-6-loaded nanoparticles with dual modifications by $PEG_{20000}$-cholesterol had a good BBB permeability, could significantly promote the passage of drug through blood-brain barrier, and had a sustained-release process.

Experiment 2

(1) Method: 6- to 8-week old male Wistar rats were randomly divided into 4 groups, with 3 rats for each group. The rats were subjected to tail vein injection with an equimolar amount of a coumarin-6 solution (a free drug), common nanoparticles loaded with coumarin-6, coumarin-6-loaded PBCA nanoparticles with single modification by $PEG_{20000}$ and coumarin-6-loaded PBCA nanoparticles with dual modifications by $PEG_{20000}$-cholesterol, respectively. The rats were killed 30 min after administration, the brain tissues were taken, and the content of coumarin-6 in brain was determined.

(2) Result: FIG. 6 (B) showed the content of coumarin-6 in the brain tissue of rats, which from left to right was the content of coumarin-6 in the brain tissue of rats injected with a free drug solution, common nanoparticles, PBCA nanoparticles with single modification by $PEG_{20000}$ and PBCA nanoparticles with dual modifications by $PEG_{20000}$-cholesterol, respectively.

As shown in the figure, as compared with the free drug solution and the common PBCA nanoparticles, the PBCA nanoparticles with single modification by $PEG_{20000}$ had the content of coumarin-6 in the brain tissue significantly increased (P<0.01). However, the PBCA nanoparticles with dual modifications by $PEG_{20000}$-cholesterol according to the invention could have the content of coumarin-6 in the brain tissue significantly increased, as compared with the PBCA nanoparticles with single modification by $PEG_{20000}$ (P<0.01). The result showed that as compared with free coumarin-6 and the coumarin-6-loaded nanoparticles with single modification by $PEG_{20000}$, the coumarin-6-loaded PBCA nanoparticles with dual modifications by PEG$_{20000}$-cholesterol had a good BBB permeability, and could promote the passage of drug through blood-brain barrier.

Example 7. Study on the Tissue Distribution of Coumarin-6-Loaded PBCA Nanoparticles with Dual Modifications by PEG$_{20000}$-Cholesterol (1) Experimental purpose: to study the tissue distribution of PBCA nanoparticles with dual modifications by PEG$_{20000}$-cholesterol in animal, and to study the toxicity in vivo.

(2) Method: 6- to 8-week old male Wistar rats were randomly divided into 3 groups, with 21 rats for each group. The rats were subjected to tail vein injection with an equimolar amount of a coumarin-6 solution (a free drug), coumarin-6-loaded nanoparticles with single modification by cholesterol and PBCA nanoparticles with dual modifications by PEG$_{20000}$-cholesterol as prepared in Example 1, respectively. The rats were killed at different time points (15 min, 30 min, 1 h, 2 h, 4 h, 8 h, 12 h) after administration, hearts, livers, spleens, lungs, and kidney tissues were taken, and the content of coumarin-6 therein was determined, respectively.

Figure 7:
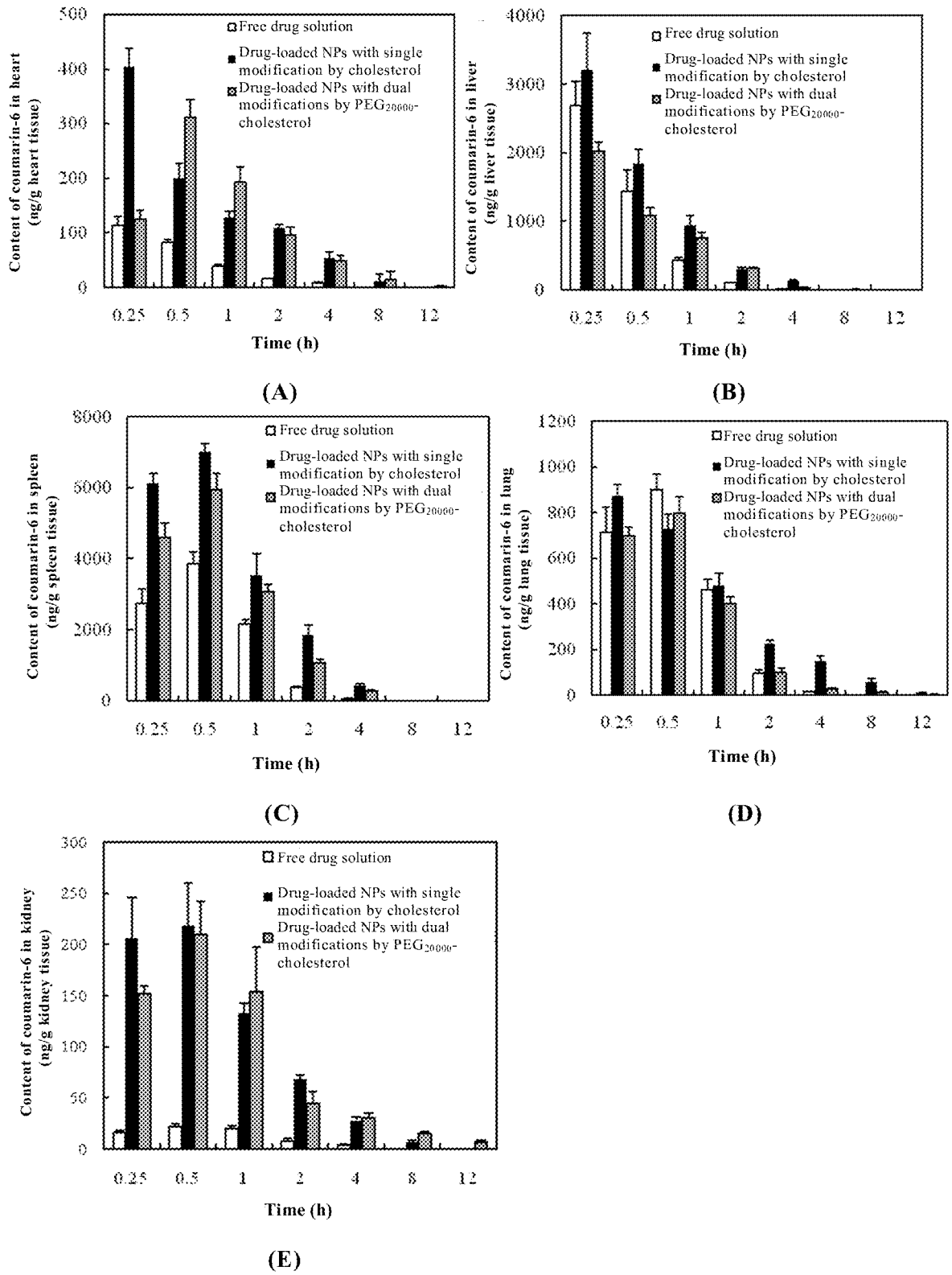
FIG. 7 shows the concentration of coumarin-6 at different time points in the tissues of rats from different groups in Example 7. As seen from the figure, the nanoparticles with dual modifications by $PEG_{20000}$-cholesterol were not significantly accumulated in various tissues and visceral organs as compared with the nanoparticles with single modification by cholesterol, and had the content of coumarin-6 in liver and spleen significantly lower than that of the nanoparticles with single modification. The result showed that the coumarin-6-loaded PBCA nanoparticles with dual modifications by $PEG_{20000}$-cholesterol had better safety in vivo.

(3) Result: FIG. 7 showed the concentration of coumarin-6 at different time points in the tissues of rats from different groups. As seen from the figure, the nanoparticles with dual modifications by PEG$_{20000}$-cholesterol were not significantly accumulated in various tissues and organs as compared with the nanoparticles with single modification by cholesterol, and had a significantly lower content in the liver and spleen as compared with the nanoparticles with single modification. The result showed that the coumarin-6-loaded PBCA nanoparticles with dual modifications by PEG$_{20000}$-cholesterol had better safety in vivo.

Example 8. Study on the In Vitro Safety of Coumarin-6-Loaded PBCA Nanoparticles with Dual Modifications by PEG$_{20000}$-Cholesterol (1) Experimental purpose: to study the cytotoxicity of PBCA nanoparticles with dual modifications by PEG$_{20000}$-cholesterol (2) Experimental method: MTT method was used to determine the cell viability.

The particular steps were as followed: bEnd.3 cells (mouse brain microvascular endothelial cells) in the logarithmic growth phase were digested and counted, and then seeded to a 96-well plate at a density of $5 \times 10^4$/well. After incubation in a 5% CO$_2$, 37° C. incubator for 24 h, the old medium was pipetted off, and media (200 µL) containing cholesterol, PEG$_{20000}$ and PBCA at a series of concentrations (5, 10, 20, 50, 100, 200, 500 and 1000 µg/ml), and media (200 µL) containing blank PBCA nanoparticles with dual modifications by PEG$_{20000}$-cholesterol and coumarin-6-loaded PBCA nanoparticles with dual modifications by PEG$_{20000}$-cholesterol at a series of concentrations (1, 2, 5, 10, 20, 50, 100 and 200 µg/ml) were added, respectively. After further incubation for 24 h and 48 h, respectively, the old medium was pipetted off, and a medium containing 0.5 mg/ml MTT was added to each well. After further incubation for 4 h, the medium was pipetted off, and washing with PBS was performed twice. DMSO (200 µl) was added to dissolve the formazan crystal, and shaking was performed in dark for 10 min; and then the OD value of each well at 490 nm was determined by ELISA instrument. The OD value of the cells incubated without the addition of drug was used as control (100%), and the cell viability for each drug groups were calculated, so as to study the proliferation state of cells, wherein 5 parallel wells were set for each group.

Figure 8:
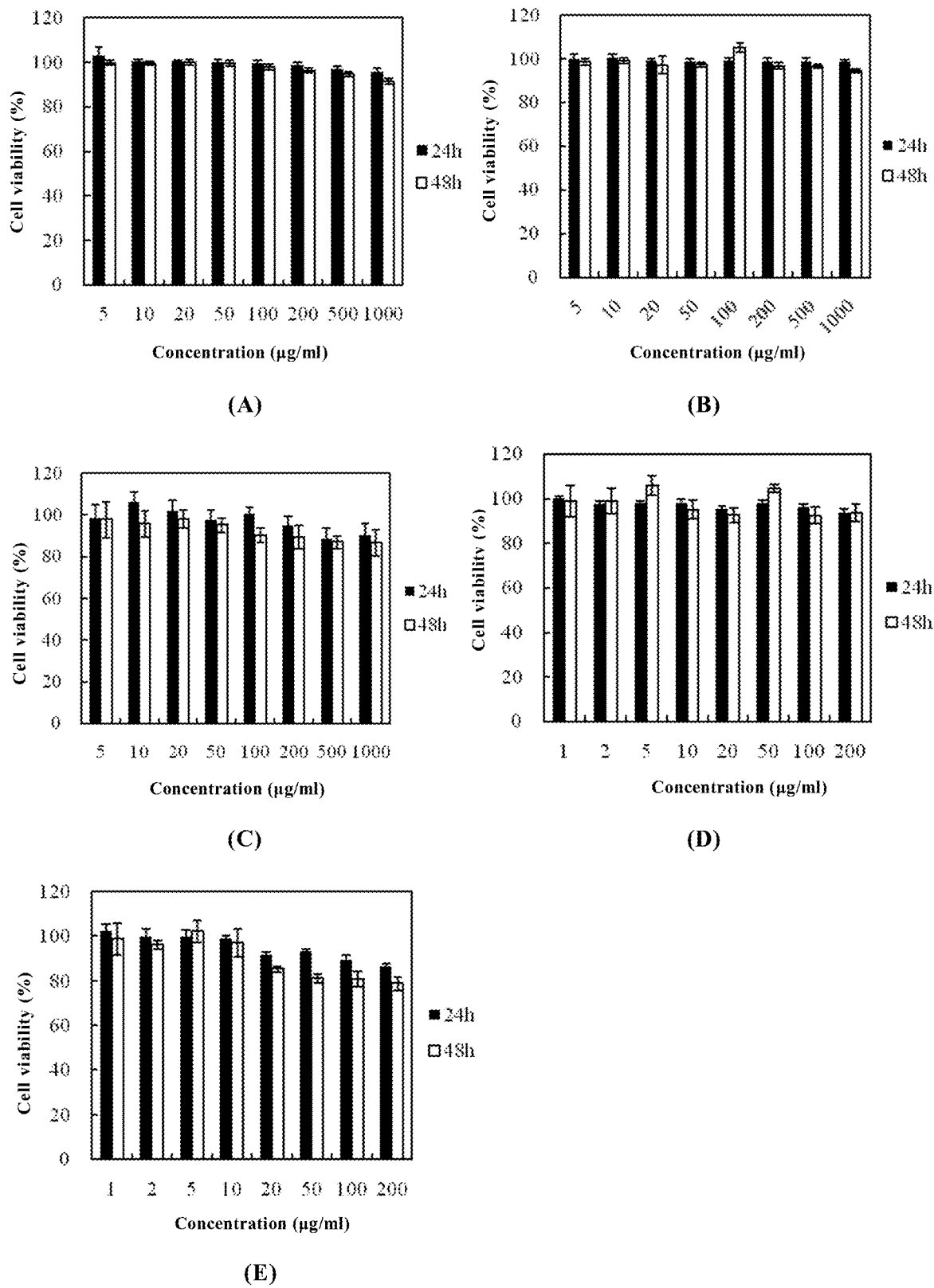
FIG. 8 shows the cell viability of bEnd.3 cells after administration of (A) cholesterol, (B) $PEG_{20000}$, (C) PBCA, (D) blank PBCA nanoparticles with dual modifications by $PEG_{20000}$-cholesterol, and (E) coumarin-6-loaded PBCA nanoparticles with dual modifications by $PEG_{20000}$-cholesterol in Example 8, respectively. In the figure, the abscissa represents the administration concentration, and the ordinate represents the cell viability. As shown in the figure, cholesterol, $PEG_{20000}$, PBCA, blank nanoparticles and coumarin-6-loaded PBCA nanoparticles with dual modifications by $PEG_{20000}$-cholesterol had no significant cytotoxicity for bEnd.3 cells with the experimental concentration range (cell viability >80%). The result showed that the blank carrier and the PBCA nanoparticles with dual modifications by $PEG_{20000}$-cholesterol had good safety in vitro.

(3) Experimental result: FIG. 8 showed the cell viability of bEnd.3 cells after administration of (A) cholesterol, (B) PEG$_{20000}$, (C) PBCA, (D) blank PBCA nanoparticles with dual modifications by PEG$_{20000}$-cholesterol, and (E) coumarin-6-loaded PBCA nanoparticles with dual modifications by PEG$_{20000}$-cholesterol, respectively. In the figure, the abscissa represents the administration concentration, and the ordinate represents the cell viability.

As shown in the figure, cholesterol, PEG$_{20000}$, PBCA, blank nanoparticles and coumarin-6-loaded PBCA nanoparticles with dual modifications by PEG$_{20000}$-cholesterol had no significant cytotoxicity for bEnd.3 cells within the experimental concentration range (cell viability >80%). The result showed that the blank nanoparticles and the PBCA nanoparticles with dual modifications by PEG$_{20000}$-cholesterol had good safety in vitro.

Example 9. Study on the Pharmacokinetics of Docetaxel-Loaded PBCA Nanoparticles with Dual Modifications by PEG$_{20000}$-Cholesterol (1) Experimental purpose: docetaxel, a medicine for treating breast cancer and non-small cell lung cancer, was generally administered via intravenous drop infusion in clinic, and could not penetrate across blood-brain barrier easily.

The purpose of this experiment was to load the PBCA nanoparticles with dual modifications by PEG$_{20000}$-cholesterol according to the invention with a drug that could not penetrate across blood-brain barrier easily, so as to observe the sustained-release of the drug after intravenous injection, wherein docetaxel was used as an example.

(2) Method: by the method as described in Example 1, docetaxel-loaded PBCA nanoparticles with dual modifications by PEG$_{20000}$-cholesterol were prepared and characterized. The docetaxel-loaded PBCA nanoparticles with dual modifications by PEG$_{20000}$-cholesterol had a narrow particle size distribution, an average particle size of 200.7 nm, a PDI of 0.122, and a Zeta potential of −2.11 mV; and the entrapment efficiency was 98.8%, and the drug loading rate was 2.13%.

6- to 8-week old male Wistar rats were subjected to jugular vein catheterization. The rats were recovered for at least 12 h after the operation, and then was randomly divided into 2 groups, with 6 rats for each group. The rats were administered with a docetaxel solution (a free drug) and docetaxel-loaded PBCA nanoparticles with dual modifications by PEG$_{20000}$-cholesterol, respectively. Blood (200 µl) was collected at the site where jugular vein catheterization was performed, at different time points after administration. After treatment, the content of docetaxel in the blood was determined by HPLC.

Figure 9:
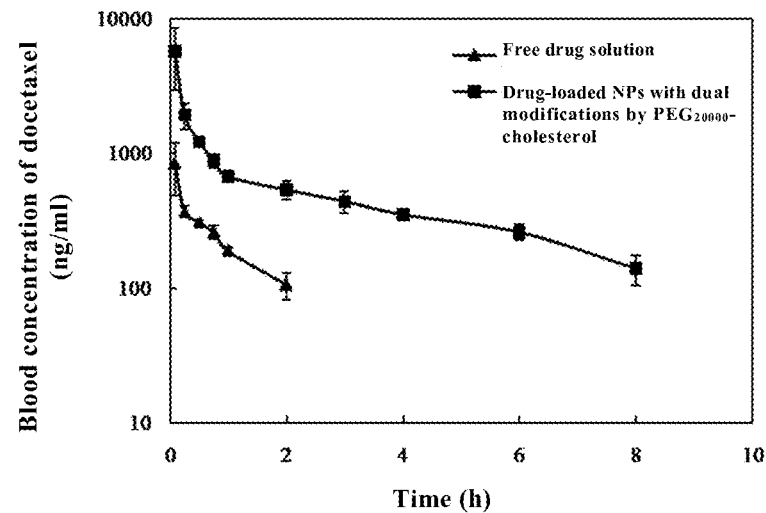
FIG. 9 shows the blood concentration—time curves after the rats were intravenously administered with a free drug solution of docetaxel and docetaxel-loaded PBCA nanoparticles with dual modifications by $PEG_{20000}$-cholesterol in Example 9 (n=6), respectively. As shown in the figure, the docetaxel-loaded PBCA nanoparticles with dual modifications by $PEG_{20000}$-cholesterol had a longer release time and a higher blood concentration in vivo.

(3) Result: FIG. 9 showed the blood concentration—time curves of a free drug solution of docetaxel and docetaxel-loaded PBCA nanoparticles with dual modifications by PEG$_{20000}$-cholesterol after intravenous administration in rats. As seen from the figure, they were significantly different. The docetaxel-loaded PBCA nanoparticles with dual modifications by PEG$_{20000}$-cholesterol could achieve the sustained-release in vivo for 8 h, whereas the free drug solution could not be detected in the blood 2 h after administration the free drug. Moreover, the docetaxel-loaded PBCA nanoparticles with dual modifications by $PEG_{20000}$-cholesterol had a higher blood concentration in vivo.

Example 10. Study on the Brain Tissue Distribution of Docetaxel-Loaded PBCA Nanoparticles with Dual Modifications by $PEG_{20000}$-Cholesterol (1) Experimental purpose: the purpose of this experiment was to load the PBCA nanoparticles with dual modifications by $PEG_{20000}$-cholesterol according to the invention with a drug that could not penetrate BBB easily, so as to observe the entry of the drug into the brain tissue via penetration across BBB after intravenous injection, wherein docetaxel was used as an example. If the concentration of docetaxel was increased in the brain tissue, it indicated that the PBCA nanoparticles with dual modifications by $PEG_{20000}$-cholesterol according to the invention had brain-targeting property, and could deliver a drug that could not easily penetrate across BBB to the brain tissue.

(2) Method: 6- to 8-week old male Wistar rats were subjected to jugular vein catheterization. The rats were recovered for at least 12 h after the operation, and then was randomly divided into 2 groups, with 6 rats for each group. The rats were subjected to tail vein injection with a docetaxel solution (a free drug), and docetaxel-loaded PBCA nanoparticles with dual modifications by $PEG_{20000}$-cholesterol, respectively. The rats were killed at different time points after administration, respectively, and the brain tissues were taken, washed with physiological saline and weighed. After treatment, the content of docetaxel in the brain tissue was determined by HPLC.

Figure 10:
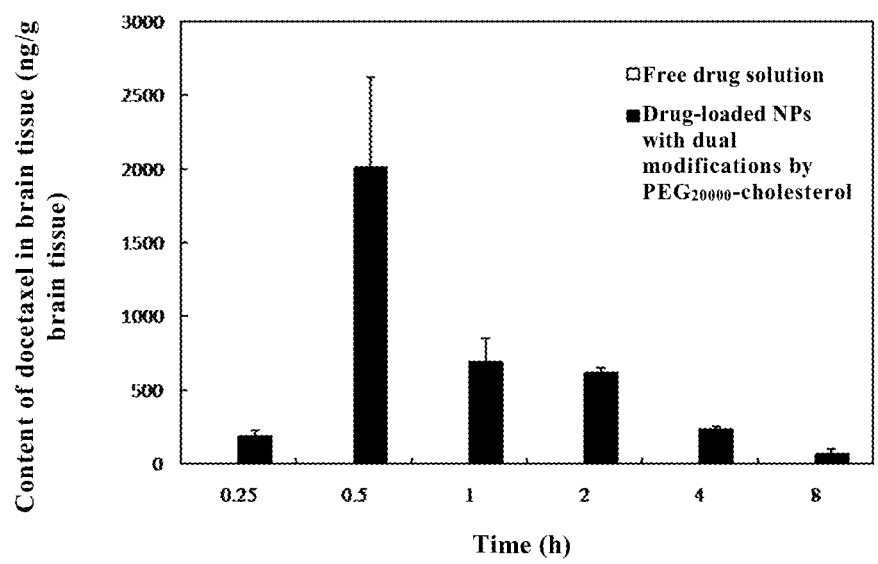
FIG. 10 shows the content of docetaxel in the brain tissue of rats after the rats were intravenously administered with a docetaxel solution (a free drug) and docetaxel-loaded PBCA nanoparticles with dual modifications by $PEG_{20000}$-cholesterol in Example 10 (n=3), respectively. As shown in the figure, docetaxel (a free drug) could hardly penetrate across the blood-brain barrier, and docetaxel was not detected in the brain; however, the docetaxel-loaded PBCA nanoparticles with dual modifications by $PEG_{20000}$-cholesterol could penetrate across the blood-brain barrier, and enabled docetaxel to be released slowly in the brain.

(3) Result: FIG. 10 showed the content of docetaxel in the brain tissue of rats at different time points after intravenous administration. As shown in the figure, after intravenous administration, docetaxel (a free drug) could hardly penetrate across blood-brain barrier, and could not be detected in the brain; however, the docetaxel-loaded PBCA nanoparticles with dual modifications by $PEG_{20000}$-cholesterol could penetrate across blood-brain barrier, so as to significantly increase the content of docetaxel in the brain tissue, and the drug could be stilled detected in the brain tissue 8 h after administration. The result showed that the PBCA nanoparticles with dual modifications by $PEG_{20000}$-cholesterol according to the invention could promote the penetration of docetaxel across blood-brain barrier, and could achieve the sustained-release of drug in the brain.

Example 11. The Inhibitory Effect of Docetaxel-Loaded PBCA Nanoparticles with Dual Modifications by $PEG_{20000}$-Cholesterol on Proliferation of Tumor Cells In Vitro (1) Experimental purpose: the purpose of this experimental is to observe the pharmacodynamical effect of a drug loaded to PBCA nanoparticles with dual modifications by $PEG_{20000}$-cholesterol by using docetaxel as an example.

(2) Method: MTT method was used to determine the proliferation state of tumor cells. The particular steps were as followed: 4T1 cells (mouse breast cancer cells) in the logarithmic growth phase were digested and counted, and then seeded to a 96-well plate at a density of $5 \times 10^4$/well. After incubation in a 5% $CO_2$, 37° C. incubator for 24 h, the old medium was pipetted off, and media (200 µL) containing docetaxel (a free drug) and docetaxel-loaded PBCA nanoparticles with dual modifications by $PEG_{20000}$-cholesterol (the administration concentration was calculated based on the amount of the loaded docetaxel) at a series of concentrations (0.0001, 0.001, 0.01, 1, 10 and 100 nmol/ml) were added, respectively. After further incubation for 24 h and 48 h, respectively, the old medium was pipetted off, and a medium containing 0.5 mg/ml MTT was added to each well. After further incubation for 4 h, the medium was pipetted off, and washing with PBS was performed twice. DMSO (200 µl) was added to dissolve the formazan crystal, and shaking was performed in dark for 10 min; and then the OD value of each well at 490 nm was determined by ELISA instrument. The OD value of the cells incubated without the addition of drug was used as control (100%), and the cell viability for each drug groups were calculated, so as to study the proliferation state of tumor cells, wherein 5 parallel wells were set for each group.

Figure 11:
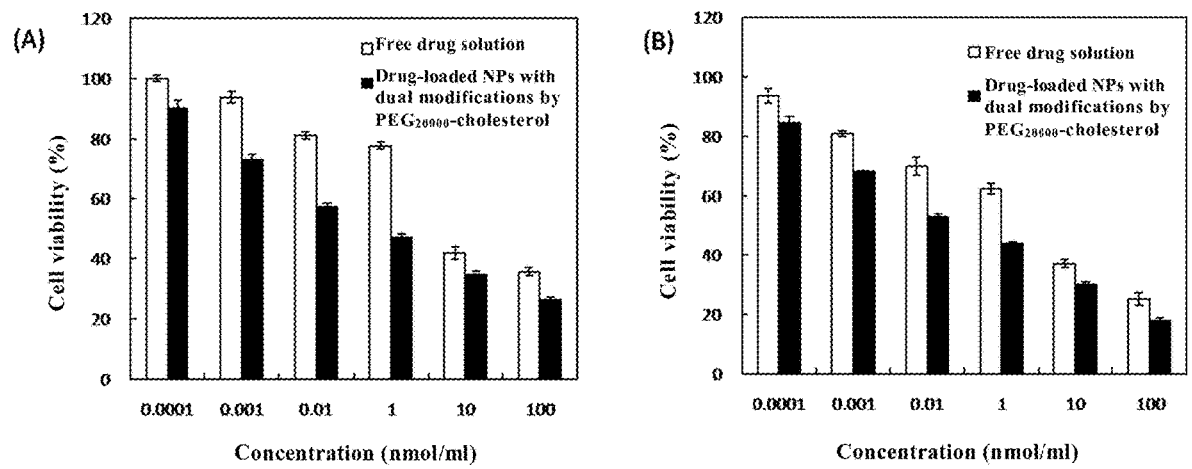
FIG. 11 shows the cell viability of mouse breast cancer 4T1 cells after separate administration of docetaxel (a free drug) and docetaxel-loaded PBCA nanoparticles with dual modifications by $PEG_{20000}$-cholesterol in Example 11. In the figure, the abscissa represents the administration concentration (calculated as the concentration of docetaxel), and the ordinate represents the cell viability; n=5; for the nanoparticles with dual modifications by $PEG_{20000}$-cholesterol, P was less than 0.01, as compared with the free drug solution. Fig. (A) and Fig. (B) show the results of incubation for 24 h and 48 h after administration, respectively. As shown in the figures, the docetaxel-loaded nanoparticles with dual modifications by $PEG_{20000}$-cholesterol had a stronger inhibitory effect on the proliferation of tumor cells as compared with free docetaxel at the same administration concentration for the same incubation time, and were dose-dependent and time-dependent to some extent.

(3) Result: FIG. 11 showed the cell viability of mouse breast cancer 4T1 cells after administration of docetaxel (a free drug) and docetaxel-loaded PBCA nanoparticles with dual modifications by $PEG_{20000}$-cholesterol, respectively. In the figure, the abscissa represents the administration concentration (calculated as the concentration of docetaxel), and the ordinate represents the cell viability. Fig. (A) and Fig. (B) showed the results of incubation for 24 h and 48 h after administration, respectively.

As shown in the figure, after administration of docetaxel-loaded nanoparticles with dual modifications by $PEG_{20000}$-cholesterol at a concentration of 0.0001 nmol/ml for 24 h, the cell viability of the tumor cells could be decreased to about 90%, whereas after the administration of docetaxel (a free drug) for 24 h, the tumor cells had no significant change in the cell viability. The docetaxel-loaded nanoparticles with dual modifications by $PEG_{20000}$-cholesterol had a stronger inhibitory effect on the proliferation of the tumor cells than free docetaxel at the administration concentration for the same incubation time, and were dose-dependent and time-dependent to some extent. A higher administration concentration and a longer the incubation time indicated a stronger inhibitory effect on the proliferation of the tumor cells.

The result showed that as compared with free docetaxel, the docetaxel-loaded nanoparticles with dual modifications by $PEG_{20000}$-cholesterol could inhibit the proliferation of the tumor cells better. As compared with the free drug solution, the drug, which was loaded to the PBCA nanoparticles with dual modification according to the invention had a better therapeutic effect, instead of a reduced efficacy.

Example 12. Preparation and Evaluation of Coumarin-6-Loaded PBCA Nanoparticles with Dual Modifications by $PEG_{20000}$-Leucine (1) Preparation method: the stabilizer Dex70 (1%, w/v) and $mPEG_{20000}$ (1.5%, w/v) were dissolved in a HCl medium (pH 1.0), and then BCA monomers (1%, v/v) were slowly added dropwise at room temperature under magnetic stirring. After stirring at 500 rpm for 4 h, coumarin-6 (1%, w/v) was added, and the stirring was performed at 750 rpm for 2.5 h. Then, the system was neutralized with NaOH to pH of 6-7, and was further stirred for 1 h so that BCA monomers were polymerized sufficiently, thereby obtaining PEG-PBCA nanoparticles. After filtration through a filtration membrane (0.45 µm), the nanoparticles obtained were lyophilized, and then re-dissolved in PBS, and mixed homogeneously for 30 min. Leucine (1%, w/v) was added, and incubation was performed for 0.5 h. After filtration and lyophilization, coumarin-6-loaded PBCA nanoparticles with dual modifications by $PEG_{20000}$-leucine were obtained and stored in a drier.

By the method above, common unmodified PBCA nanoparticles loaded with coumarin-6 were also prepared, as control.

(2) Measurement and Result of particle size and potential: by the method as described in Example 1, the coumarin-6-loaded PBCA nanoparticles with dual modifications by PEG$_{20000}$-leucine were measured for particle size and Zeta potential. The nanoparticles had an average particle size of 167.3 nm, a PDI of 0.138, and a Zeta potential of −9.63 mV.

(3) Measurement and Result of entrapment efficiency and drug loading rate: as measured by the method as described in Example 1, the entrapment efficiency and drug loading rate of coumarin-6 were 98.1% and 2.04%, respectively.

Example 13. Study on the In Vitro Release of Coumarin-6-Loaded PBCA Nanoparticles with Dual Modifications by PEG$_{20000}$-Leucine (1) Method: PBCA nanoparticles with dual modifications by PEG$_{20000}$-leucine (1 ml) were placed in a dialysis bag (MWCO: 20000, USA), and the dialysis bag was placed in 200 ml pH7.4 phosphate-buffered saline (PBS), under stirring at 100 rpm in dark in a 37° C. thermostatic water bath. The release medium (200 µl) was taken at different time points within 24 h, and meanwhile PBS was supplemented. The concentration of coumarin-6 in the release medium was determined with blank PBS used as control. For each time point, 6 samples were determined in parallel. By the same method, unmodified PBCA nanoparticles loaded with coumarin-6 were determined.

Figure 12:
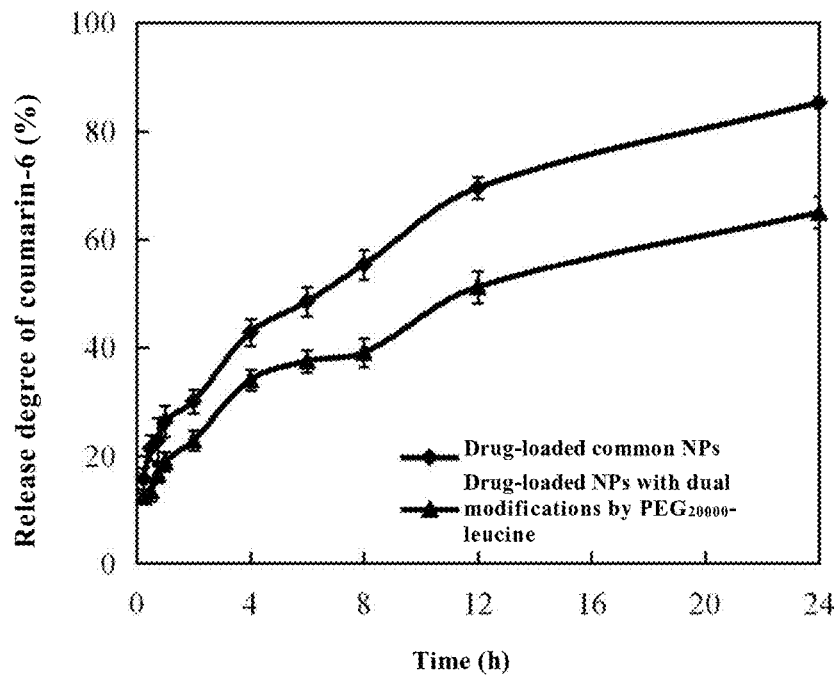
FIG. 12 shows the in vitro release curves of coumarin-6-loaded PBCA nanoparticles with dual modifications by $PEG_{20000}$-leucine, and unmodified PBCA nanoparticles loaded with coumarin-6 in Example 13 (n=6). As shown in the figure, the nanoparticles with dual modifications by $PEG_{20000}$-leucine had a more significant sustained-release property, as compared with the unmodified nanoparticle.

(2) Result: FIG. 12 showed the in vitro release curve of coumarin-6-loaded PBCA nanoparticles with dual modifications by PEG$_{20000}$-leucine, and the in vitro release curve of unmodified PBCA nanoparticles loaded with coumarin-6. As seen from the figure, the nanoparticles with dual modifications by PEG$_{20000}$-leucine were significantly different from the common nanoparticles in terms of in vitro release behavior (f2=32.88, <50). As compared with the unmodified nanoparticles, the nanoparticles with dual modifications by PEG$_{20000}$-leucine had a more significant sustained-release property, indicating a better stability, which was favorable for a better BBB permeability in vivo.

Example 14. Preparation and Evaluation of Coumarin-6-Loaded PBCA Nanoparticles with Dual Modifications by PEG$_{20000}$-Aspartic Acid (1) Preparation method: the stabilizer Dex70 (1%, w/v) and mPEG$_{20000}$ (1.5%, w/v) were dissolved in a HCl medium (pH1.0), and then BCA monomers (1%, v/v) were slowly added dropwise at room temperature under magnetic stirring. After stirring at 500 rpm for 4 h, coumarin-6 (1%, w/v) was added, and the stirring was performed at 750 rpm for 2.5 h. Then, the system was neutralized with NaOH to pH of 6-7, and was further stirred for 1 h so that BCA monomers were sufficiently polymerized, thereby obtaining PEG-PBCA nanoparticle. After filtration through a filtration membrane (0.45 µm), the nanoparticles obtained were lyophilized, and then re-dissolved in PBS, and mixed homogeneously for 30 min. L-aspartic acid (1%, w/v) was added, and incubation was performed for 0.5 h. After filtration and lyophilization, PBCA nanoparticles with dual modifications by PEG$_{20000}$-aspartic acid were obtained and stored in a drier.

By the method above, common unmodified PBCA nanoparticles loaded with coumarin-6 were also prepared, as control.

(2) Measurement and Result of particle size and potential: by the method as described in Example 1, coumarin-6-loaded PBCA nanoparticles with dual modifications by PEG$_{20000}$-aspartic acid were measured for particle size and Zeta potential. The nanoparticles had an average particle size of 146.2 nm, a PDI of 0.119, and a Zeta potential of −6.78 mV.

(3) Measurement and Result of entrapment efficiency and drug loading rate: as measured by the method as described in Example 1, the entrapment efficiency and drug loading rate of coumarin-6 were 96.9% and 1.98%, respectively.

Example 15. Study on the In Vitro Release of Coumarin-6-Loaded PBCA Nanoparticles with Dual Modifications by PEG$_{20000}$-Aspartic Acid (1) Method: coumarin-6-loaded PBCA nanoparticles with dual modifications by PEG$_{20000}$-aspartic acid (1 ml) were placed in a dialysis bag (MWCO: 20000, USA), and the dialysis bag was placed in 200 ml pH7.4 phosphate-buffered saline (PBS), under stirring at 100 rpm in dark in a 37° C. thermostatic water bath. The release medium (200 µl) was taken at different time points within 24 h, and meanwhile PBS was supplemented. The concentration of coumarin-6 in the release medium was determined with blank PBS used as control. By the same method, the unmodified PBCA nanoparticles loaded with coumarin-6 were determined.

Figure 13:
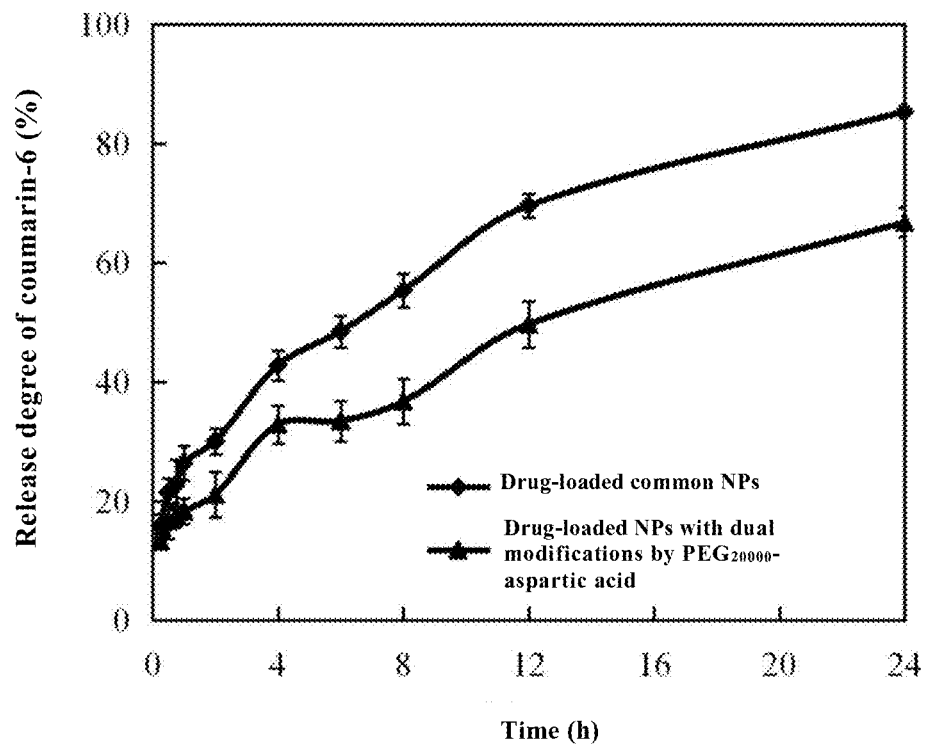
FIG. 13 shows the in vitro release curves of coumarin-6-loaded PBCA nanoparticles with dual modifications by $PEG_{20000}$-aspartic acid, and unmodified PBCA nanoparticles loaded with coumarin-6 in Example 15 (n=6). As shown in the figure, the nanoparticles with dual modifications by $PEG_{20000}$-aspartic acid had a more significant sustained-release property, as compared with the unmodified nanoparticles.

(2) Result: FIG. 13 showed the in vitro release curve of coumarin-6-loaded PBCA nanoparticles with dual modifications by PEG$_{20000}$-aspartic acid, and the in vitro release curve of unmodified PBCA nanoparticles loaded with coumarin-6. As seen from the figure, the nanoparticles with dual modifications by PEG$_{20000}$-aspartic acid were significantly different from the common nanoparticles (f2=34.32, <50). As compared with the unmodified nanoparticles, nanoparticles with dual modifications by PEG$_{20000}$-aspartic acid had a more significant sustained-release property, indicating a better stability, which was favorable for a better BBB permeability in vivo.

Example 16. Preparation and Evaluation of Coumarin-6-Loaded PBCA Nanoparticles with Dual Modifications by PEG$_{20000}$-Lecithin (1) Preparation method: the stabilizer Dex70 (1%, w/v) and mPEG$_{20000}$ (1.5%, w/v) were dissolved in a HCl medium (pH 1.0), and then BCA monomers (1%, v/v) were slowly added dropwise at room temperature under magnetic stirring. After stirring at 500 rpm for 4 h, coumarin-6 (1%, w/v) was added, and the stirring was performed at 750 rpm for 2.5 h. Then, the system was neutralized with NaOH to pH of 6-7, and was further stirred for 1 h so that BCA monomers were sufficiently polymerized, thereby obtaining PEG-PBCA nanoparticle. After filtration through a filtration membrane (0.45 µm), the nanoparticles obtained were lyophilized, and then re-dissolved in PBS and mixed homogeneously for 30 min. Lecithin (1%, w/v) was added, and incubation was performed for 0.5 h. After filtration and lyophilization, coumarin-6-loaded PBCA nanoparticles with dual modifications by PEG$_{20000}$-lecithin were obtained and stored in a drier.

By the method above, common unmodified PBCA nanoparticles loaded with coumarin-6 were prepared, as control.

(2) Measurement and Result of particle size and potential: by the method as described in Example 1, coumarin-6-loaded PBCA nanoparticles with dual modifications by PEG$_{20000}$-lecithin were measured for particle size and Zeta potential. The nanoparticles had an average particle size of 344.2 nm, a PDI of 0.252, and a Zeta potential of −37.3 mV.

(3) Measurement and Result of entrapment efficiency and drug loading rate: as measured by the method described in Example 1, the entrapment efficiency and drug loading rate of coumarin-6 were 97.4% and 1.95%, respectively.

Example 17. Study on In Vitro Release of PBCA Nanoparticles with Dual Modifications by PEG$_{20000}$-Lecithin (1) Method: coumarin-6-loaded PBCA nanoparticles with dual modifications by PEG$_{20000}$-lecithin (1 ml) were placed in a dialysis bag (MWCO: 20000, USA), and the dialysis bag was placed in 200 ml pH7.4 phosphate-buffered saline (PBS), under stirring at 100 rpm in dark in a 37° C. thermostatic water bath. The release medium (200 μl) was taken at different time points within 24 h, and meanwhile PBS was supplemented. B The concentration of coumarin-6 in the release medium was determined with blank PBS used as control. At each time point, 6 samples were determined in parallel.

Figure 14:
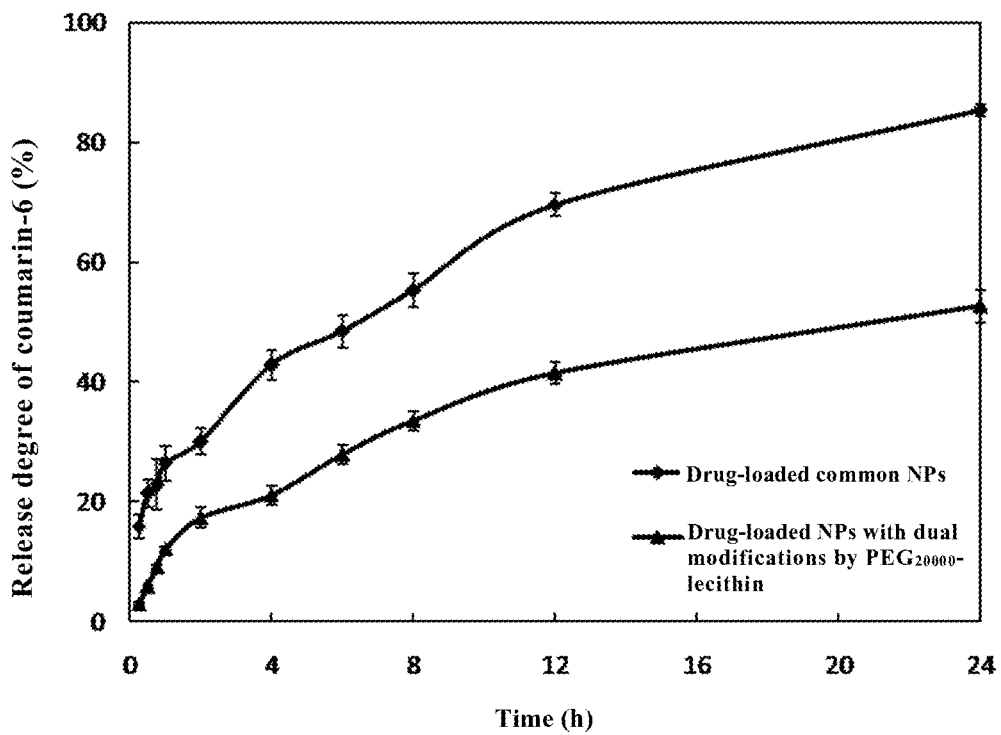
FIG. 14 the in vitro release curves of coumarin-6-loaded PBCA nanoparticles with dual modifications by $PEG_{20000}$-lecithin, and unmodified PBCA nanoparticles loaded with coumarin-6 in Example 17 (n=6). As shown in the figure, the nanoparticles with dual modifications by $PEG_{20000}$-lecithin had a more significant sustained-release property, as compared with the unmodified nanoparticles.

(2) Result: FIG. 14 showed the in vitro release curve of coumarin-6-loaded PBCA nanoparticles with dual modifications by PEG$_{20000}$-lecithin, and the in vitro release curve of unmodified PBCA nanoparticles loaded with coumarin-6. As shown in the figure, the nanoparticles with dual modifications by PEG$_{20000}$-lecithin were significantly different from the common nanoparticles in terms of in vitro release behavior (f2=30.98, <50). As compared with the unmodified nanoparticles, the nanoparticles with dual modifications by PEG$_{20000}$-lecithin had a more significant sustained-release property, indicating a better stability, which was favorable for a better BBB permeability in vivo.

Example 18. Study on the Brain Tissue Distribution of PBCA Nanoparticles with Dual Modifications by Different Modifiers (1) Experimental purpose: to study the brain-targeting property of PBCA nanoparticles with dual modifications by different modifiers in animal.

(2) Method: 6- to 8-week-old male Wistar rats were randomly divided into 5 groups, with 3 rats for each group. The rats were subjected to tail vein injection with an equimolar amount of a coumarin-6 solution (a free drug), common nanoparticles loaded with coumarin-6, coumarin-6-loaded PBCA nanoparticles with dual modifications by PEG$_{20000}$-leucine, coumarin-6-loaded PBCA nanoparticles with dual modifications by PEG$_{20000}$-aspartic acid and coumarin-6-loaded PBCA nanoparticles with dual modifications by PEG$_{20000}$-lecithin, respectively. The rats were killed 30 min after administration, the brain tissues was taken, and the content of coumarin-6 in brain was determined.

Figure 15:
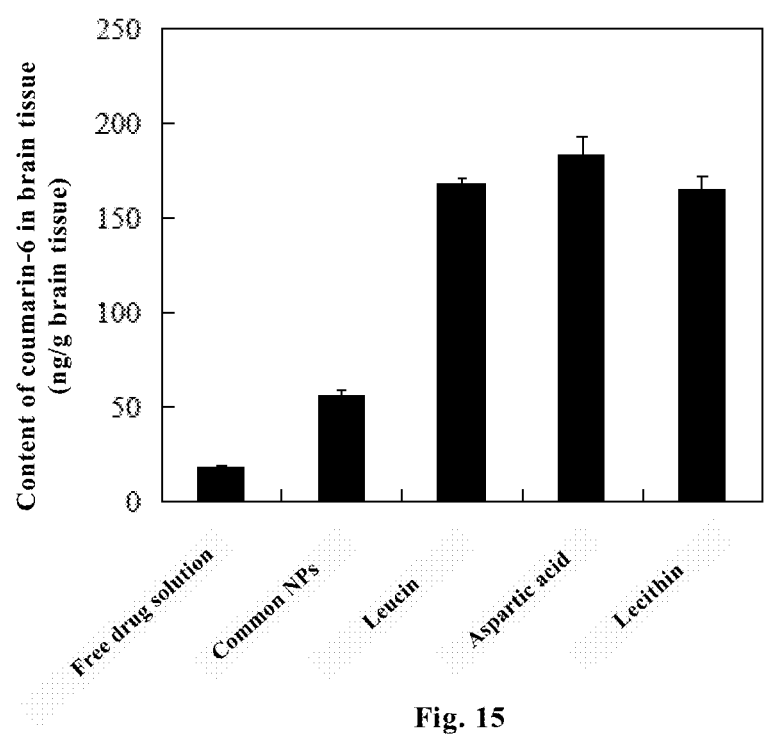
FIG. 15 shows the content of coumarin-6 in the brain tissue of the rats injected with different samples in Example 18, wherein the samples from left to right were a free drug solution, common nanoparticles, PBCA nanoparticles with dual modifications by $PEG_{20000}$-leucine, PBCA nanoparticles with dual modifications by $PEG_{20000}$-aspartic acid, and PBCA nanoparticles with dual modifications by $PEG_{20000}$-lecithin, respectively. For the three nanoparticles with dual modifications, P<0.01 as compared with the free drug solution and the common nanoparticles. As shown in the figure, as compared with the free drug solution and the common PBCA nanoparticles, the three nanoparticles with dual modifications according to the invention might have a significantly increased content of coumarin-6 in the brain tissue, and enhance the BBB permeability of drug.

(3) Result: FIG. 15 showed the content of coumarin-6 in the brain tissue of rats, which from left to right was the content of coumarin-6 in the brain tissue of the rats injected with a free drug solution, common nanoparticles, PBCA nanoparticles with dual modifications by PEG$_{20000}$-leucine, PBCA nanoparticles with dual modifications by PEG$_{20000}$-aspartic acid and PBCA nanoparticles with dual modifications by PEG$_{20000}$-lecithin, respectively.

As shown in the figure, as compared with the free drug solution and the common PBCA nanoparticles, the three nanoparticles with dual modification according to the invention might have a significantly increased content of coumarin-6 in the brain tissue (P<0.01). The result showed that all of the three PBCA nanoparticles with dual modification had a good BBB permeability, and could significantly promote the passage of drug through blood-brain barrier

Example 19. Preparation of PBCA Nanoparticles with Dual Modifications by PEG$_{20000}$-Lecithin The stabilizer Dex70 (1%, w/v) and mPEG$_{20000}$ (1.5%, w/v) were dissolved in a HCl medium (pH 1.0), and then BCA monomers (1%, v/v) were slowly added dropwise at room temperature under magnetic stirring. After stirring at 500 rpm for 4 h, the system was neutralized with NaOH to pH of 6-7, and was further stirred for 1 h so that BCA monomers were sufficiently polymerized, thereby obtaining PEG-PBCA nanoparticles. After filtration through a filtration membrane (0.45 μm), the nanoparticles obtained were lyophilized, and then were re-dissolved in PBS, and mixed homogeneously for 30 min. Lecithin (1%, w/v) was added, and incubation was performed for 0.5 h. After filtration and lyophilization, PBCA nanoparticles with dual modifications by PEG$_{20000}$-lecithin were obtained and stored in a drier.

As seen from the experimental results in the Examples above, the PBCA nanoparticles with dual modification according to the invention had good BBB permeability. By loading the PBCA nanoparticles with dual modification according to the invention with a drug that could not penetrate across the BBB easily, it could significantly increase the content of the drug in the brain tissue of animal, and bring about a better sustained-release behavior, which was favorable for enhancing safety and efficacy of drugs. A drug delivery system comprising the drug-loaded nanoparticle could be used in manufacture of a brain-targeting formulation, and had a good application value in the diagnosis, prevention and/or treatment of a central nervous system disease (including but not limited to brain tumor).

Although the embodiments of the invention have been described in detail, a person skilled in the art would understand that according to all the disclosed teachings, details can be amended and modified, and these alterations all fall into the protection scope of the invention. The scope of the invention is defined by the attached claims and any equivalent thereof.

The invention claimed is:

1. A nanoparticle, comprising poly(n-butyl cyanoacrylate), wherein the nanoparticle is modified with a first modifier and a second modifier on the surface, wherein the first modifier is polyethylene glycol, and the second modifier is lecithin or cholesterol; and wherein the polyethylene glycol has a number-average molecular weight of 2000-20000.

2. A method for preparing the nanoparticle according to claim 1, comprising the following steps:
   Step 1: n-butyl cyanoacrylate monomers are subjected to a polymerization reaction in an acidic medium comprising a first modifier;
   Step 2: a base is added to the reaction mixture of Step 1 until the reaction mixture is neutral, the reaction mixture is filtrated, and the filtrate is lyophilized;
   Step 3: the lyophilized product is dispersed in a buffer, a second modifier is added, and incubation is performed; and
   Step 4: nanoparticles are separated from the mixture of Step 3.

3. A drug delivery system comprising the nanoparticle according to claim 1, wherein the nanoparticle is loaded with a drug.

4. A method for preparing the drug delivery system according to claim 3, comprising the following steps:
  Step 1: n-butyl cyanoacrylate monomers are subjected to a polymerization reaction in an acidic medium comprising a first modifier;
  Step 2: a drug is added to the reaction mixture, and then the polymerization reaction is further performed;
  Step 3: a base is added to the reaction mixture until the reaction mixture is neutral, the reaction mixture is filtrated, and the filtrate is lyophilized;
  Step 4: the lyophilized product is dispersed in a buffer, a second modifier is added, and incubation is performed; and
  Step 5: nanoparticles are separated from the mixture of Step 4.

5. A pharmaceutical composition, comprising the nanoparticle according to claim 1, and a pharmaceutically acceptable carrier and/or excipient, wherein the nanoparticle is loaded with a drug.

6. A method for enhancing the ability of a drug to penetrate across the blood brain barrier in a subject, comprising loading the nanoparticle according to claim 1 with the drug.

7. A method for promoting drug penetration across the blood brain barrier in a subject, comprising loading the nanoparticle according to claim 1 with a drug, and administering the drug to the subject.

8. The nanoparticle according to claim 1, having one or more features selected from the following:
  (1) the nanoparticle has an average particle size of 50-800 nm;
  (2) the nanoparticle has a polydispersity index of 0.100-0.300;
  (3) the nanoparticle has a Zeta potential of −100-0 mV;
  (4) the first modifier and the polycyanoacrylate have a mass ratio of 0.5%-5%;
  (5) the second modifier and the polycyanoacrylate have a mass ratio of 0.05%-2%;
  (6) the concentration of the second modifier on the surface of the nanoparticle is $5\times10^{-7}$ ng/nanoparticle-$1\times10^{-6}$ ng/nanoparticle;
  (7) the nanoparticle is prepared by a method comprising the following steps:
  Step 1: n-butyl cyanoacrylate monomers are subjected to a polymerization reaction in an acidic medium comprising a first modifier;
  Step 2: a base is added to the reaction mixture of Step 1 until the reaction mixture is neutral, the reaction mixture is filtrated, and the filtrate is lyophilized;
  Step 3: the lyophilized product is dispersed in a buffer, a second modifier is added, and incubation is performed; and
  Step 4: nanoparticles are separated from the mixture of Step 3.

9. The drug delivery system according to claim 3, having one or more features selected from the following:
  (1) the drug is encapsulated in the nanoparticle;
  (2) in the drug delivery system, the nanoparticle has a drug entrapment efficiency of 80%-100%;
  (3) the drug delivery system has a drug loading rate of 1%-10%; and
  (4) the drug delivery system is prepared by a method comprising the following steps:
  Step 1: n-butyl cyanoacrylate monomers are subjected to a polymerization reaction in an acidic medium comprising a first modifier;
  Step 2: a drug is added to the reaction mixture, and then the polymerization reaction is further performed;
  Step 3: a base is added to the reaction mixture until the reaction mixture is neutral, the reaction mixture is filtrated, and the filtrate is lyophilized;
  Step 4: the lyophilized product is dispersed in a buffer, a second modifier is added, and incubation is performed; and
  Step 5: nanoparticles are separated from the mixture of Step 4.

10. The drug delivery system according to claim 3, wherein the drug is a paclitaxel drug or a fluorescent substance.

11. A nanoparticle, comprising poly(n-butyl cyanoacrylate), wherein the nanoparticle is modified with a first modifier and a second modifier on the surface, wherein the first modifier is polyethylene glycol, and the second modifier is aspartic acid or leucine; wherein the polyethylene glycol has a number-average molecular weight of 2000-20000; and wherein the nanoparticle excludes polysorbate 80.

12. A drug delivery system comprising the nanoparticle according to claim 11, wherein the nanoparticle is loaded with a drug.

13. The drug delivery system according to claim 12, wherein the drug is a paclitaxel drug or a fluorescent substance.

14. A pharmaceutical composition, comprising the nanoparticle according to claim 11, and a pharmaceutically acceptable carrier and/or excipient, wherein the nanoparticle is loaded with a drug.

15. The nanoparticle according to claim 11, having one or more features selected from the following:
  (1) the nanoparticle has an average particle size of 50-800 nm;
  (2) the nanoparticle has a polydispersity index of 0.100-0.300;
  (3) the nanoparticle has a Zeta potential of −100-0 mV;
  (4) the first modifier and the polycyanoacrylate have a mass ratio of 0.5%-5%;
  (5) the second modifier and the polycyanoacrylate have a mass ratio of 0.05%-2%;
  (6) the concentration of the second modifier on the surface of the nanoparticle is $5\times10^{-7}$ ng/nanoparticle-$1\times10^{-6}$ ng/nanoparticle; and
  (7) the nanoparticle is prepared by a method comprising the following steps:
  Step 1: n-butyl cyanoacrylate monomers are subjected to a polymerization reaction in an acidic medium comprising a first modifier;
  Step 2: a base is added to the reaction mixture of Step 1 until the reaction mixture is neutral, the reaction mixture is filtrated, and the filtrate is lyophilized;
  Step 3: the lyophilized product is dispersed in a buffer, a second modifier is added, and incubation is performed; and
  Step 4: nanoparticles are separated from the mixture of Step 3.

* * * * *